US007375180B2

(12) United States Patent
Gorden et al.

(10) Patent No.: US 7,375,180 B2
(45) Date of Patent: May 20, 2008

(54) METHODS AND COMPOSITIONS RELATED TO IRM COMPOUNDS AND TOLL-LIKE RECEPTOR 8

(75) Inventors: Keith B. Gorden, Maplewood, MN (US); Xiaohong Qiu, Rosemount, MN (US); John P. Vasilakos, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 203 days.

(21) Appl. No.: 10/777,310

(22) Filed: Feb. 12, 2004

(65) Prior Publication Data
US 2004/0162309 A1    Aug. 19, 2004

Related U.S. Application Data

(60) Provisional application No. 60/447,179, filed on Feb. 13, 2003.

(51) Int. Cl.
*A61K 38/00* (2006.01)

(52) U.S. Cl. .......................... 530/300; 530/350; 435/6; 435/7.1

(58) Field of Classification Search .................... None
See application file for complete search history.

(56) References Cited

U.S. PATENT DOCUMENTS

| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,376,501 A | 12/1994 | Mariën et al. |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,605,899 A | 2/1997 | Gerster et al. |
| 5,693,811 A | 12/1997 | Lindstrom |
| 5,741,908 A | 4/1998 | Gerster et al. |
| 5,756,747 A | 5/1998 | Gerster |
| 5,939,090 A | 8/1999 | Beaurline et al. |
| 6,028,076 A | 2/2000 | Hirota et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,113,918 A | 9/2000 | Johnson et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,303,347 B1 | 10/2001 | Johnson et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,376,501 B1 | 4/2002 | Isobe et al. |
| 6,376,669 B1 | 4/2002 | Rice et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,810 B1 | 9/2002 | Coleman et al. |
| 6,476,000 B1 | 11/2002 | Agrawal |
| 6,514,985 B1 | 2/2003 | Gerster et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |

(Continued)

FOREIGN PATENT DOCUMENTS

| EP | 0 394 026 | 10/1990 |
| EP | 1 104 764 A1 | 6/2001 |
| JP | 9-208584 | 8/1997 |
| JP | 11-80156 | 3/1999 |
| JP | 11-222432 | 8/1999 |

(Continued)

OTHER PUBLICATIONS

Saunder et al. (Antimicrobial Agents and Chemotherapy, Dec. 2003, vol. 47, No. 12, pp. 3846-3852).*
Gorden et al. (Journal of Immunology, 2005, vol. 174, pp. 1259-1268).*
Dockrell et al. (J. of Antimicrobial Chemotherapy (2001), vol. 48, pp. 751-755).*

(Continued)

*Primary Examiner*—Hope Robinson

(57) ABSTRACT

Methods of eliciting a TLR8-mediated cellular response are disclosed. Such methods include administration of either a TLR8 agonist or a TLR8 antagonist to an IRM-responsive cell so that the IRM compound affects at least one TLR8-mediate cellular signaling pathway. In some cases, the method may provide prophylactic or therapeutic treatment for a condition treatable by modulating a TLR8-mediated cellular pathway.

17 Claims, 8 Drawing Sheets

U.S. PATENT DOCUMENTS

| | | |
|---|---|---|
| 6,558,951 B1 | 5/2003 | Tomai et al. |
| 6,573,273 B1 | 6/2003 | Crooks et al. |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 7,179,253 B2 | 2/2007 | Graham et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0110840 A1 | 8/2002 | Tomai et al. |
| 2003/0022302 A1 | 1/2003 | Lewis et al. |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0199461 A1 | 10/2003 | Averett et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0171086 A1* | 9/2004 | Fink et al. .................. 435/7.2 |

FOREIGN PATENT DOCUMENTS

| | | |
|---|---|---|
| JP | 2000-247884 | 9/2000 |
| WO | WO 00/47719 A2 | 8/2000 |
| WO | WO 00/75304 A1 | 12/2000 |
| WO | WO 00/76505 A1 | 12/2000 |
| WO | WO 00/76518 A1 | 12/2000 |
| WO | WO 01/74343 A2 | 10/2001 |
| WO | WO 02/22809 | 3/2002 |
| WO | WO 02/36592 A1 | 5/2002 |
| WO | WO 02/46188 A2 | 6/2002 |
| WO | WO 02/46189 A2 | 6/2002 |
| WO | WO 02/46190 A2 | 6/2002 |
| WO | WO 02/46191 A2 | 6/2002 |
| WO | WO 02/46192 A2 | 6/2002 |
| WO | WO 02/46193 A2 | 6/2002 |
| WO | WO 02/46194 A2 | 6/2002 |
| WO | WO 02/46749 A2 | 6/2002 |
| WO | WO 02/085905 A1 | 10/2002 |
| WO | WO 02/102377 A1 | 12/2002 |
| WO | WO 03/020889 A2 | 3/2003 |
| WO | WO 03/043572 A2 | 5/2003 |
| WO | WO 03/045391 A1 | 6/2003 |
| WO | WO 03/089602 | 10/2003 |
| WO | WO 03/103584 A2 | 12/2003 |

OTHER PUBLICATIONS

Richarson (J. of Org. Chem., vol. 25, p. 2581, 1963).*

Akira S. et al., "Recognition of pathogen-associated molecular patterns by TLR family", *Immunology Letters*, 2003, vol. 85, pp. 85-95.

Ozinsky A. et al., "The repertoire for pattern recognition of pathogens by the innate immune system is defined by cooperation between Toll-like receptors", *Proc. Nat. Acad. Sci.*, Dec. 2000, vol. 97, No. 25, pp. 13766-13771.

Lee et al., "Saturated Fatty Acid Activates but Polyunsaturated Fatty Acid Inhibits Toll-like Receptor 2 Dimerized with Toll-like Receptor 6 or 1", *The Journal of Biological Chemistry*, vol. 279, No. 17, pp. 16971-16979.

Fonteneau et al., "Human Immunodeficiency Virus Type 1 Activates Plasmacytoid Dendritic Cells and Concomitantly Induces the Bystander Maturation of Myeloid Dendritic Cells", *Journal of Virology*, vol. 78, No. 10, pp. 5223-5232.

Testerman, et al., "Cytokine Induction by the Immunomodulators Imiquimod and S-27609", *Journal of Leukocyte Biology*, vol. 58, pp. 365-372, Sep. 1995.

Chollet, et al, "Development of a Topically Active Imiquimod Formulation", *Pharmaceutical Development and Technology*, 4(1), pp. 35-43 (1999).

Brassard et al.; "Interferon-α as an immunotherapeutic protein"; Journal of Leukocyte Biology; vol. 71; Apr. 2002; pp. 565-581.

Izumi et al.; "1$H$-imidazo[4,5-$c$]quinoline Derivatives as Novel Potent TNF-α Suppressors: Synthesis and Structure-Activity Relationship of 1-, 2-and 4-Substituted 1$H$-imidazo[4,5-$c$]quinolines or 1$H$-imidazo[4,5-$c$]pyridines"; *Bioorganic and Medicinal Chemistry*, vol. 11, pp. 2541-2550 (2003).

Hornung et al., "Quantitative Expression of Toll-Like Receptor 1-10 mRNA in Cellular Subsets of Human Peripheral Blood Mononuclear Cells and Sensitivity to CpG Oligodeoxynucleotides[1]", *The Journal of Immunology*, 2002, 168; pp. 4531-4537.

Hemmi et al., "Small anti-viral compounds activate immune cells via the TLR7 MyD88-dependent Signaling pathway", *Nature Immunology*, vol. 3, No. 2; Feb. 2002; pp. 196-200.

Medzhitov, "Toll-Like Receptors and Innate Immunity", *Nature Reviews Immunology*, vol. 1; Nov. 2001, pp. 135-145.

Jurk et al. "Human TLR7 and TLR8 independently confer responsiveness to the antiviral compound R-848", *Nature Immunology*, Jun. 2002, vol. 3, No. 6; p. 1.

Akira et al., "Toll-like receptors: critical proteins linking innate and acquired immunity", *Nature Immunology*, Aug. 2001, vol. 2, No. 8; pp. 675-680.

Heil et al.; "Synthetic immunostimulatory compounds activate immune cells via TLR7 and TLR8"; 33th Annual Meeting of the Deutsche Gessellschaft für Immunologie, Marburg 2002—Abstract C.6.

Jurk et al. Nature immunology 2, 499 (2002).

* cited by examiner

US 7,375,180 B2

METHODS AND COMPOSITIONS RELATED TO IRM COMPOUNDS AND TOLL-LIKE RECEPTOR 8

CROSS-REFERENCE TO RELATED APPLICATION

This application claims priority to U.S. Provisional Patent Application No. 60/447,179, filed Feb. 13, 2003.

BACKGROUND

There has been a major effort in recent years, with significant success, to discover new drug compounds that act by stimulating certain key aspects of the immune system, as well as by suppressing certain other aspects (see, e.g., U.S. Pat. Nos. 6,039,969 and 6,200,592). These compounds, referred to herein as immune response modifiers (IRMs), appear to act through basic immune system mechanisms known as Toll-like receptors (TLRs) to induce selected cytokine biosynthesis. They may be useful for treating a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis, melanoma), and $T_H 2$-mediated diseases (e.g., asthma, allergic rhinitis, atopic dermatitis, multiple sclerosis), and are also useful as vaccine adjuvants.

Many of the IRM compounds are small organic molecule imidazoquinoline amine derivatives (see, e.g., U.S. Pat. No. 4,689,338), but a number of other compound classes are known as well (see, e.g., U.S. Pat. Nos. 5,446,153; 6,194,425; and 6,110,929) and more are still being discovered. Other IRMs have higher molecular weights, such as oligonucleotides, including CpGs (see, e.g., U.S. Pat. No. 6,194,388).

In view of the great therapeutic potential for IRMs, and despite the important work that has already been done, there is a substantial ongoing need to expand their uses and therapeutic benefits.

SUMMARY

It has been found that many IRM compounds act through Toll-Like Receptor (TLR) pathways, including pathways mediated by TLR8.

The present invention provides methods of eliciting a TLR8-mediated cellular response in a cell that expresses TLR8. The methods include selecting a compound identified as either a TLR8 agonist or a TLR8 antagonist and administering to the cell the compound in an amount that affects at least one TLR8-mediated cellular signaling pathway.

In another aspect, the present invention provides methods of treating an organism having a condition treatable by modulating a TLR8-mediated cellular response. The methods include selecting a compound identified as either a TLR8 agonist or a TLR8 antagonist and administering to the organism the compound in an amount effective to modulate a TLR8-mediated cellular signaling pathway.

In yet another aspect, the present invention provides methods of identifying a TLR8 agonist. The methods include a) exposing a TLR8-positive cell culture to a test compound and measuring a TLR8-mediated cellular response; b) exposing a TLR8-negative cell culture to a test compound and measuring a TLR8-mediated cellular response; and c) identifying the test compound as a TLR8 agonist if the cellular response in the TLR8-positive cell culture is greater than the cellular response of the TLR8-negative cell culture.

In yet another aspect, the present invention provides compounds identified as IRM compounds by the method described above; and pharmaceutical compositions that include a compound identified as a TLR8 agonist by the method described above in combination with a pharmaceutically acceptable carrier.

In yet another aspect, the present invention provides methods of identifying a TLR8 antagonist. The methods include a) exposing a first IRM-responsive cell culture to a TLR8 agonist and measuring a TLR8-mediated cellular response; b) exposing a second IRM-responsive cell culture to a TLR8 agonist and a test compound, and measuring a TLR8-mediated cellular response; and c) identifying the test compound as an TLR8 antagonist if the cellular response in the first cell culture is greater than the cellular response of the second cell culture.

In yet another aspect, the present invention provides TLR8 antagonist compounds identified by the method described above; and pharmaceutical compositions that include a compound identified as a TLR8 antagonist by the method described above in combination with a pharmaceutically acceptable carrier.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Figure 1:
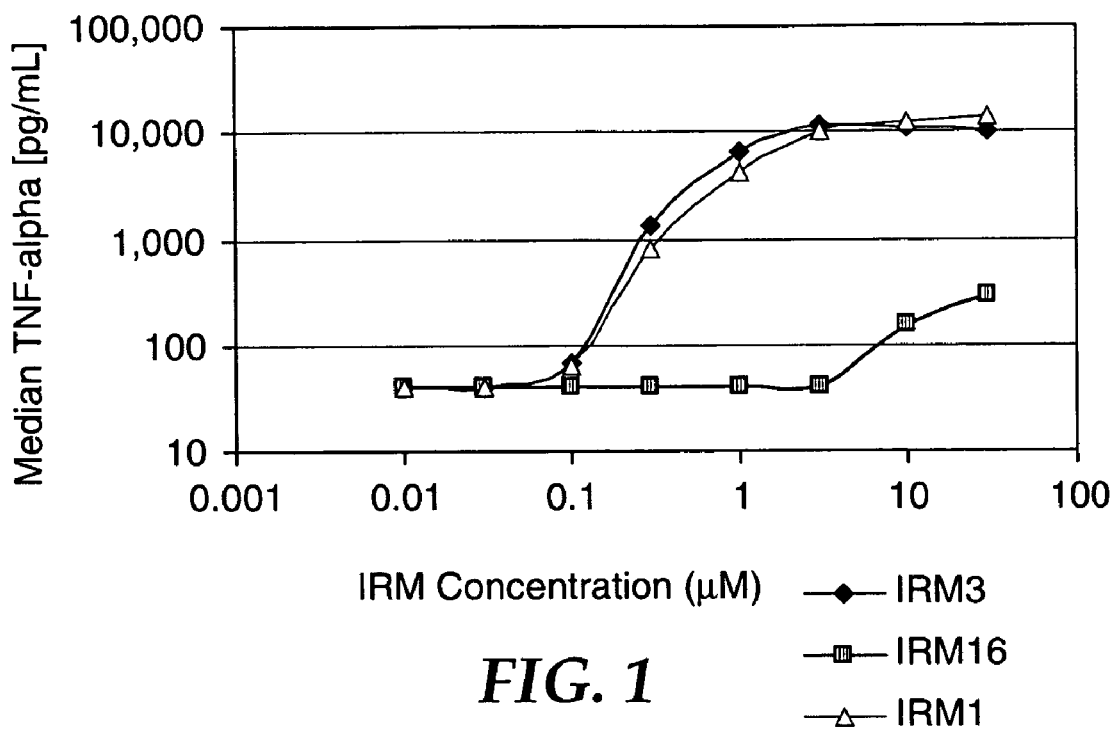
FIG. 1 is a line graph showing induction of TNF-α in human monocytes by TLR8 agonists.

The present invention provides methods of detecting compounds that act as agonists of TLR8. The present invention also provides methods of identifying compounds that act as antagonists of TLR8.

A compound identified as either a TLR8 agonist or a TLR8 antagonist may be employed to elicit a TLR8-mediated cellular response. Accordingly, the present invention provides methods of eliciting a TLR8-mediated cellular response. Such cellular responses can include altering, for example, cytokine production, NF-κB activation, and/or expression of co-stimulatory markers.

Certain conditions may be treatable by altering a TLR8-mediated cellular response. Accordingly, the present invention also provides methods of treating an organism having a condition treatable by modulating a TLR8-mediated cellular response. Such conditions include, for example, neoplastic diseases, $T_H1$-mediated diseases, $T_H2$-mediated diseases, and infectious diseases (e.g., viral diseases, bacterial diseases, fungal diseases, parasitic diseases, protozoal diseases, prion-mediated diseases, and the like).

For purposes of this invention, the following terms shall have the meanings set forth as follows:

"Agonist" refers to a compound that, in combination with a receptor (e.g., a TLR), can produce a cellular response. An agonist may be a ligand that directly binds to the receptor. Alternatively, an agonist may combine with a receptor indirectly by, for example, (a) forming a complex with another molecule that directly binds to the receptor, or (b) otherwise resulting in the modification of another compound so that the other compound directly binds to the receptor. An agonist may be referred to as an agonist of a particular TLR (e.g., a TLR8 agonist).

"Cellular signaling pathway" refers to a cascade of biochemical activity that biochemically links an agonist-receptor combination with a cellular response to the agonist-receptor binding (e.g., cytokine production).

"Dominant negative" refers to a variant of a naturally occurring protein in which the variant has been altered to possess at least one natural activity, but lack at least one other natural activity. As a nonlimiting example, a dominant negative variant of a receptor protein may bind to its normal binding partner (e.g., a ligand) but fail to promote a second activity that normally results from the receptor-ligand binding (e.g., relay a cellular signal).

"Express" and variations thereof refer, generally, to the ability of a cell to transcribe a structural gene, resulting in an mRNA, and then translating the mRNA to form a protein that provides a detectable biological function to the cell.

"Inhibit" refers to any measurable reduction of biological activity. Thus, as used herein, "inhibit" or "inhibition" may be referred to as a percentage of a normal level of activity.

"IRM antagonist" refers to any compound that inhibits biological activity that normally results from exposing an IRM-responsive cell to an IRM compound.

"IRM compound" refers to a compound that alters the level of one or more immune regulatory molecules, e.g., cytokines or co-stimulatory markers, when administered to an IRM-responsive cell. Representative IRM compounds include the small organic molecules, purine derivatives, small heterocyclic compounds, amide derivatives, and oligonucleotide sequences described below.

"IRM-responsive cell" refers to any cell that exhibits a cellular response when exposed to an IRM compound.

"TLR8-mediated" refers to a biological or biochemical activity that results from TLR8 function.

"TLR8-negative" refers to a cell culture selected to provide less detectable TLR8 function than a corresponding TLR8-positive cell culture. A TLR8-negative cell culture may exhibit less than normal TLR8 function, e.g., inhibited TLR8 function compared to a TLR8-positive cell culture exhibiting generally normal TLR8 function. Alternatively, a TLR8-negative cell culture may exhibit generally normal or greater than normal TLR8 function, e.g., a cell culture exhibiting generally normal TLR8 function compared to a TLR8-positive cell culture exhibiting greater than normal TLR8 function.

"TLR8-positive" refers to a cell culture selected to provide greater detectable TLR8 function than a corresponding TLR8-negative cell culture. A TLR8-positive cell culture may exhibit greater than normal TLR8 function, e.g., overexpression of TLR8 function compared to a TLR8-negative cell culture exhibiting generally normal TLR8 function. Alternatively, a TLR8-positive cell culture may exhibit generally normal or less than normal TLR8 function, e.g., a cell culture exhibiting generally normal TLR8 function compared to a TLR8-negative cell culture exhibiting inhibited TLR8 function.

Certain cells of the immune system (e.g., antigen presenting cells, or "APCs") recognize foreign antigens, some of which potentially may be harmful to the host, and trigger an immune response against the antigen. Toll-Like Receptors (TLRs) are a family of immune system receptors that permit cells of the immune system to recognize specific molecular patterns presented by foreign antigens. The molecular patterns are commonly termed pathogen-associated molecular patterns ("PAMPs"). The TLRs include an extracellular domain that contains a leucine-rich domain and a cytoplasmic domain that resembles the cytoplasmic domain of the interleukin-1 receptor.

Activation of the various TLRs induces a range of biological effects including the secretion of cytokines and antimicrobial peptides. Cytokines are important immune system regulatory molecules and include, but are not limited to, TNF-α, Type I interferons, and the interleukins. Cytokines act upon cellular receptors and regulate such diverse cellular activities as cell growth, cell differentiation, cell death, the inflammatory process, and cell migration.

The discovery of different TLRs has led to the identification of signaling pathways that connect the receptors to the biological effects of their activation. The cytoplasmic protein MyD88 has been identified as one member of cellular signaling pathways that also include various TLRs. The MyD88 protein has an IL-1 receptor domain similar to that of the cytoplasmic domain of the TLRs. The IL-1 receptor domain of the MyD88 and the cytoplasmic TLR domain interact when the TLR binds to a ligand and, in turn, cause other cytoplasmic proteins (e.g., IRAK and TRAF6) to interact. The signal cascade that begins with an agonist binding to a TLR and is relayed through IRAK and TRAF6 eventually activates NF-κB, which stimulates transcription of various genes including those encoding cytokines such as TNF-α, IL-6, and IL-12.

Many IRM compounds share a number of cellular activities, many of which are conserved across species, e.g., upregulation of co-stimulatory markers, induction of proinflammatory cytokines in monocyte/macrophage cells, and activation of transcriptional regulators NF-κB and AP-1. At least some of these cellular activities are mediated by TLR8. Identifying TLR8 agonists, including but not limited to IRM compounds, may identify compounds having prophylactic or therapeutic utility for certain conditions that are treatable by inducing an immune response through TLR8.

Table 2 shows that a broad spectrum of IRM compounds can induce NF-κB activation through TLR8. HEK293 cells, derived from human embryonic kidney cells, may be co-transfected with (1) either a control vector (HEK293-vector) or a vector construct including human TLR8 (HEK293-TLR8), and (2) an NF-κB-luciferase reporter. The NF-κB-luciferase reporter provides a luciferase signal upon NF-κB activation in a transfected cell. Thus, TLR8-mediated NF-κB activity can be detected by exposing the cells transfected with vector and the cells transfected with the TLR8 construct to a test compound, then comparing the luciferase signal of the vector-transfected cells with the luciferase signal of the cells transfected with the TLR8 construct. The test compound may be considered a TLR8 agonist if the luciferase signal induced from the TLR8-transfected cells is greater than the luciferase signal induced from the vector-transfected cells.

Table 2 shows that various IRM compounds stimulate NF-κB activity in transfected cells to varying degrees, ranging up to more than a ten-fold increase in NF-κB activation over cells transfected with only vector. In some embodiments, a compound may be identified as a TLR8 agonist if the compound, at a concentration of 10 μM, induces at least a two-fold increase in NF-κB activation in HEK293-TLR8 cells over a vehicle control. In other embodiments, a compound may be identified as a TLR8 agonist if the compound, at a concentration of about 30 μM or less, induces at least a five-fold increase in NF-κB activation in HEK293-TLR8 cells over a vehicle control.

A dominant-negative variant of TLR8 (TLR8DN) may be employed to identify agonists of TLR8. A TLR8DN can be used to identify TLR8 agonists such as, for example, IRM compounds. A broad range of compounds may be screened in this fashion to identify agonists of TLR8.

A TLR8 agonist also can be identified by employing TLR8-specific antibodies that neutralize TLR8 function. Cells that express TLR8 may be preincubated with anti-TLR8 antibodies and then incubated with various stimuli. A test compound may be identified as a TLR8 agonist if the cellular response induced by the test compound is inhibited by TLR8-specific antibodies to a greater extent than the cellular response is inhibited when the TLR8-expressing cells are stimulated with an agonist of another TLR (e.g., the TLR4 agonist LPS). Overexpression of TLR8 also can be used to identify a TLR8 agonist. Cells transfected with a vector that encodes TLR8 expressed from a strong eukaryotic promoter can be incubated with a test compound. If the transfected cells provide a greater TLR8-mediated cellular response than an appropriate control cell culture, the test compound may be identified as a TLR8 agonist.

The present invention provides assays that can be used to discover new IRM compounds that can activate or inhibit at least one TLR8-mediated pathway. The assays described below are exemplary embodiments of the invention and are not intended to represent the limits of the invention.

The present invention provides methods for identifying a TLR8 agonist that include determining whether a particular compound elicits a TLR8-mediated cellular response. One way this can be done is by eliminating or reducing the activity of TLR8 in a cell and measuring the resulting effect of reducing or eliminating TLR8 activity on at least one TLR8-mediated cellular response.

In some embodiments, the methods of the present invention include transfecting an IRM-responsive cell with a dominant-negative variant of TLR8 to eliminate or to measurably reduce TLR8-mediated activity upon exposure of the transfected cell to a TLR8 agonist. A compound that induces a reduced TLR8-mediated cellular response in the dominant-negative variant may be identified as a TLR8 agonist.

A dominant-negative variant of TLR8 (TLR8DN) can be constructed in various ways. In some embodiments, a TLR8DN can be made by altering the cytoplasmic domain of the protein, thereby disrupting binding between TLR8 and its cytoplasmic binding partners. In other embodiments, TLR8 may be altered to disrupt the interaction between TLR8 and a TLR8 agonist. Regardless of the specific change made in TLR8, a dominant-negative variant will be unable to relay a TLR8-mediated cellular signal when exposed to a TLR8 agonist.

A mutation resulting in a TLR8DN may be a point mutation, a deletion or an insertion. A deletion or insertion may be of any size. In some of these embodiments, the mutation can be non-conservative. In other embodiments, the mutation can be conservative. In yet other embodiments, the mutation at the DNA level may form a stop codon, resulting in a truncated protein. Alternatively, the mutation may cause a shift in the reading frame that changes the amino acid sequence downstream from the frameshift mutation.

One method of identifying a TLR8 agonist includes exposing a TLR8-positive cell culture to a test compound and measuring a TLR8-mediated cellular response; exposing a TLR8-negative cell culture to the test compound and measuring a TLR8-mediated cellular response; and identifying the compound as a TLR8 agonist if the cellular response in the TLR8-positive cell culture is greater than the cellular response of the TLR8-negative cell culture.

The step of exposing a TLR8-positive cell culture to a test compound and measuring a TLR8-mediated cellular response may include exposing a control IRM-responsive cell culture (e.g., cells transfected with a null vector) to the test compound, measuring the TLR8-mediated cellular response of the control culture, and comparing the cellular response of the TLR8-positive test culture to the cellular response of the control culture. Similarly, the step of exposing a TLR8-negative cell culture to a test compound and measuring a TLR8-mediated cellular response may include exposing a control IRM-responsive cell culture to the test compound, measuring the TLR8-mediated cellular response in the control culture, and comparing the cellular response of the TLR8-negative test culture to the cellular response of the control culture. However, with experience, one skilled in the art may develop sufficient familiarity with a particular assay that explicit use of controls may not always be necessary to identify a TLR8 agonist using the methods of the present invention.

In some embodiments, the TLR8-positive cell culture may include cells that provide a greater than normal IRM-mediated cellular response. For example, the TLR8-positive cell culture may include cells that have been genetically modified, such as by transfection, to provide a greater than normal IRM-mediated response when stimulated with an IRM. Such genetic modifications may include providing additional copies of TLR8 structural genes so that transfected cells overexpress TLR8. Additionally, overexpression of TLR8 may result from cloning a TLR8 structural gene under the control of one or more strong transcriptional regulatory sequences.

The TLR8-positive cell culture may include transfected cells that overexpress TLR8. Cells that express or overexpress TLR8 can be made by various standard techniques (See, e.g., *Current Protocols in Molecular Biology*, John Wiley and Sons, Inc. (2001)). In embodiments in which the TLR8-positive cell culture provides a greater than normal TLR8-mediated cellular response, the TLR8-negative cell culture may include cells that provide a generally normal level TLR8-mediated cellular response. Alternatively, the TLR8-negative cell culture may include cells that provide a lower than normal TLR8-mediated cellular response.

In other embodiments, the TLR8-positive cell culture may include cells that provide a generally normal TLR8-mediated cellular response. In such embodiments, the TLR8-negative cell culture includes cells that provide a lower than normal TLR8-mediated cellular response. In such embodiments, the TLR8-negative cell culture may include cells that have been genetically modified to provide the lower than normal TLR8-mediated response when stimulated with a TLR8 agonist. For example, the TLR8-negative cell culture may include cells that have been transfected with a vector that encodes a dominant-negative TLR8 variant (TLR8DN). In other embodiments, the TLR8-negative cell culture may include cells that have been transfected with vectors that include antisense constructs of TLR8 to at least partially inhibit expression of TLR8. See, e.g., *Current Protocols in Molecular Biology*, John Wiley and Sons, Inc. (2001).

Alternatively, the TLR8-negative cell culture may include one or more inhibitory components that interfere with either (1) binding of the test compound with TLR8, or (2) the ability of TLR8 to relay a cellular signal after binding to an agonist (i.e., the test compound). For example, the TLR8-negative cell culture may include an antibody that specifically binds to TLR8 (an anti-TLR8 antibody, generally), thereby at least partially inhibiting the TLR8-mediated cellular response. The generation of an antibody that specifically binds to a particular target is considered routine to one skilled in the art. Thus, an anti-TLR8 antibody can be used to provide a TLR8-negative cell culture according to the methods of the present invention.

In certain embodiments, an anti-TLR8 antibody may be used to provide a TLR8-negative cell culture. The anti-TLR8 antibody may be added to the cell culture prior to the test compound or may be added with the test compound. The anti-TLR8 antibody may be polyclonal or monoclonal. The final concentration of antibody in the cell culture may be any concentration that provides a desired reduction in TLR8 function. In some exemplary embodiments, the anti-TLR8 antibody may be present in a range from about 0.01 µg/ml to about 100 µg/ml. In embodiments in which the cells of the cell culture are pre-incubated in the presence of the anti-TLR8 antibody, the pre-incubation may range from about 0 minutes to about 48 hours prior to addition of the test compound.

In some embodiments, the TLR8-mediated cellular response may include production of at least one cytokine including, but not limited to, TNF-α, a Type I interferon (e.g., IFN-α, IFN-β, IFN-ω, etc.), IFN-γ, IL-1, IL-6, IL-8, IL-10, IL-12, MIP-1, MCP-1, or any combination thereof. In other embodiments, the TLR8-mediated cellular response may include activation of NF-κB. In still other embodiments, the TLR8-mediated cellular response may include production of one or more co-stimulatory markers (e.g., CD40, CD80, CD86, etc.), an intercellular adhesion molecule (ICAM, e.g., ICAM-1, ICAM-2, I-CAM-3, etc.), or a maturation marker such as, for example, CCR7.

Typically, cells in which TLR8 and/or expression has been at least partially inhibited will exhibit at least a 20% reduction in the extent to which administration of a TLR8 agonist stimulates TLR8-mediated activity (e.g., cytokine production or NF-κB activation) compared to untransfected cells stimulated with the same concentration of test compound. In certain embodiments the cells may exhibit at least a 50% reduction in the extent to which administration of a TLR8 agonist stimulates TLR8-mediated activity. In other embodiments, at least an 80% reduction is observed.

In one embodiment, the method may be designed to identify an agonist of TLR8 by employing a TLR8 overexpression cell culture as a TLR8-positive cell culture, an unmodified cell culture as a TLR8-negative cell culture, and measure a TLR8-mediated cellular response in each cell culture after stimulation with a test compound. In an alternative embodiment identifying a TLR8 agonist, the method may employ an unmodified cell culture as a TLR8-positive cell culture, and either a TLR8DN cell culture or a cell culture that includes anti-TLR8 antibodies as the TLR8-negative cell culture.

Thus, the present invention provides compounds identified as agonists of TLR8. Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

The present invention also provides pharmaceutical compositions that include a TLR8 agonist. Pharmaceutical compositions may include one or more additional components such as, for example, a pharmaceutically acceptable vehicle, one or more adjuvants, one or more pharmaceutically active compounds (i.e., the TLR8 agonist may serve as an adjuvant), and the like.

The present invention also provides methods of identifying a TLR8 antagonist. Such methods include exposing a first IRM-responsive cell culture to a TLR8 agonist and measuring an TLR8-mediated cellular response; exposing a second IRM-responsive cell culture to the TLR8 agonist and a test compound and measuring an TLR8-mediated cellular response; and identifying the test compound as a TLR8 antagonist if the cellular response in the first cell culture is greater than the cellular response in the second cell culture.

In order to identify antagonists of TLR8, the IRM-responsive cell culture should include cells that express TLR8. In certain embodiments, the cell culture may include cells that naturally express one or more additional TLRs. Alternatively, the IRM-responsive cell culture may include cells that do not express any additional TLRs, such as many of the TLR8-positive cell cultures described above.

As with the identification methods described above, the identification of TLR8 antagonist compounds may include the use of a control cell culture against which the TLR8-mediated cellular response of the first IRM-responsive cell culture and second IRM-responsive cell culture are compared. However, once again, one skilled in the art may develop sufficient familiarity with the assay that running a control for each assay may become unnecessary.

The concentration of the test compound being assayed by the above methods may range, for example, from about 0.001 µM to about 100 µM, although in some embodiments the assay may be performed with a test compound present in concentrations outside this range. The cell culture may be incubated with the test compound, for example, from about 10 minutes to about 24 hours, although in some cases the incubation period may be outside this range. The density of cells incubated with the compound to be tested may be, for example, from about $1 \times 10^4$ to about $1 \times 10^7$ cells/ml, although in some embodiments the assay may be performed using a cell culture having a cell density outside this range.

In some embodiments, cytokine levels are determined using a commercially available ELISA assay. In other embodiments, cytokine levels are determined using such techniques as, for example, antibody detection and quantitation (e.g., flow cytometry, western blotting, immunohisto/cytochemistry, proteome array assays), and bioassays (e.g., L929 cytotoxicity assay where the amount of cell death is directly proportional to the amount of TNF-α in the sample). See, e.g., *Current Protocols in Immunology*, John Wiley and Sons, Inc. (2001).

IRM-responsive cells used in the above-described methods may be from plants or from animals. In some embodiments, the IRM-responsive cells may be from mammals such as, for example, human, rodent, dog, cat, sheep, cow, or rabbit. These IRM-responsive cells may include, but are not limited to, monocytes, macrophages, Langerhans cells, dendritic cells, polymorphonuclear leukocytes (e.g., neutrophils, basophils and/or eosinophils), B lymphocytes, or any combination of cell types that include at least one of the foregoing. The IRM-responsive cells may be from established cell lines such as RAW 264.7 (mouse macrophage cells, available from American Type Tissue Collection, Manassas, Va., ATCC No. TIB-71), THP-1 (human monocyte cells derived from acute monocytic leukemia tissue; available from American Type Culture Collection, Manassas, Va., ATCC No. TIB-202), or HEK293 (immortalized human embryonic kidney cells, available from American Type Culture Collection, Manassas, Va., ATCC No. CRL-1573).

The TLR8 genes utilized in the methods may be obtained from or be derived from any one of a variety of plant and animal sources including mammals such as, for example, human, rodent, dog, cat, sheep, cow, or rabbit.

The expression of TLR8 in cells employed in the methods of the present invention may result from natural gene expression in the cells. Cells that naturally express TLR8 include, but are not limited to, monocytes, macrophages, B lymphocytes, polymorphonuclear leukocytes, and dendritic cells. Alternatively, the expression of TLR8 may result from the genetic modification of cells. The cells so modified may naturally express TLR8 or they may lack natural expression of TLR8. For example, unmodified HEK293 cells do not detectably express TLR8. The expression of TLR8 in cells employed in the methods of the present invention may be at a level higher than, lower than, similar to, or equal to the normal level of expression of TLR8 in the particular line of cells.

Many different cytokines and/or markers can be assayed in the methods described above. Suitable measurable cytokines include, but are not limited to, TNF-α, a Type I interferon, IFN-γ, IL-1, IL-6, IL-8, IL-10, IL-12, MIP-1, and MCP-1. Suitable measurable markers co-stimulatory markers include (e.g., CD40, CD80, CD86), intercellular adhesion molecules (ICAMs, e.g., ICAM-1, ICAM-2, I-CAM-3, etc.), and maturation markers such as, for example, CCR7.

A compound identified as a TLR8 agonist or a TLR8 antagonist by any of the methods described above, or identified by any other method, may be employed to elicit TLR8-mediated cellular responses. As used herein, the term "elicit" includes upregulation or downregulation of a particular cellular response. A compound identified as a TLR8 agonist or a TLR8 antagonist by any of the methods described above, or identified by any other method, also may be used to treat an organism having a condition treatable by modulating (i.e., either upregulating or downregulating) a TLR8-mediated cellular response.

The present invention also provides methods of eliciting a TLR8-mediated cellular response by manipulating a TLR8-mediated signaling pathway. Certain TLR8-mediated cellular responses elicited by the methods of the present invention include induction of cytokine production or co-stimulatory marker production; other cellular responses include inhibiting production of certain cytokines or co-stimulatory markers.

The invention provides a method of eliciting at least one TLR8-mediated cellular response in an IRM-responsive cell by administering to the IRM-responsive cells an IRM compound that affects at least one TLR8-mediated cellular signaling pathway.

IRM compounds include compounds that possess potent immunomodulating activity including but not limited to antiviral and antitumor activity. Certain IRMs modulate the production and secretion of cytokines. For example, certain IRM compounds induce the production and secretion of cytokines such as, e.g., Type I interferons, TNF-α, IL-1, IL-6, IL-8, IL-10, IL-12, MIP-1, and/or MCP-1. As another example, certain IRM compounds can inhibit production and secretion of certain $T_H2$ cytokines, such as IL-4, IL-5, and IL-13. Additionally, some IRM compounds are said to suppress IL-1 and TNF (U.S. Pat. No. 6,518,265).

Certain IRMs are small organic molecules (e.g., molecular weight under about 1000 Daltons, preferably under about 500 Daltons, as opposed to large biological molecules such as, for example, proteins, peptides, and the like) such as those disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,545,016; 6,545,017; 6,558,951; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; European Patent 0 394 026; U.S. Patent Publication Nos. 2002/0016332; 2002/0055517; 2002/0110840; 2003/0133913; 2003/0199538; and 2004/0014779; and International Patent Publication Nos. WO 02/102377 and WO 03/103584.

Additional examples of small molecule IRMs include certain purine derivatives (such as those described in U.S. Pat. No. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/085905), and certain 3-β-D-ribofuranosylthiazolo[4,5-d]pyrimidine derivatives (such as those described in U.S. Patent Publication No. 2003/0199461).

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG and are described, for example, in International Patent Publication No. WO 00/75304.

IRM compounds suitable for use as TLR8 agonists include compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

In certain embodiments, the IRM compound may be an imidazonaphthyridine amine; a tetrahydroimidazonaphthyridine amine; an oxazoloquinoline amine; a thiazoloquinoline amine; an oxazolopyridine amine; a thiazolopyridine amine; an oxazolonaphthyridine amine; a thiazolonaphthyridine amine; a 6-, 7-, 8-, or 9-aryl or heteroaryl substituted imidazoquinoline amine; or a 1H-imidazo dimer fused to pyridine amine, quinoline amine, tetrahydroquinoline amine, naphthyridine amine, or tetrahydronaphthyridine amine.

In certain embodiments, the IRM compound may be a substituted imidazoquinoline amine; a tetrahydroimidazoquinoline amine; an imidazopyridine amine; a 1,2-bridged imidazoquinoline amine; a 6,7-fused cycloalkylimidazopyridine amine; an imidazonaphthyridine amine; a tetrahydroimidazonaphthyridine amine; an oxazoloquinoline amine; a thiazoloquinoline amine; an oxazolopyridine amine; a thiazolopyridine amine; an oxazolonaphthyridine amine; a thiazolonaphthyridine amine; a 6-, 7-, 8-, or 9-aryl or heteroaryl substituted imidazoquinoline amine; or a 1H-imidazo dimer fused to a pyridine amine, quinoline amine, tetrahydroquinoline amine, naphthyridine amine, or tetrahydronaphthyridine amine.

As used herein, a substituted imidazoquinoline amine refers to an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amine, or a 6-, 7-, 8-, or 9-aryl or heteroaryl substituted imidazoquinoline amine. As used herein, substituted imidazoquinoline amines specifically and expressly exclude 1-(2-methylpropyl)-1H-imidazo[4,5-c]quinolin-4-amine and 4-amino-α,α-dimethyl-2-ethoxymethyl-1H-imidazo[4,5-c]quinolin-1-ethanol.

In one particular embodiment, the TLR8 agonist is an amide substituted imidazoquinoline amine. In an alternative embodiment, the TLR8 agonist is a sulfonamide substituted imidazoquinoline amine. In another alternative embodiment, the TLR8 agonist is a urea substituted imidazoquinoline amine. In another alternative embodiment, the TLR8 agonist is an aryl ether substituted imidazoquinoline amine. In another alternative embodiment, the TLR8 agonist is a heterocyclic ether substituted imidazoquinoline amine. In another alternative embodiment, the TLR8 agonist is an amido ether substituted imidazoquinoline amine. In another alternative embodiment, the TLR8 agonist is a sulfonamido ether substituted imidazoquinoline amine. In another alternative embodiment, the TLR8 agonist is a urea substituted imidazoquinoline ether. In another alternative embodiment, the TLR8 agonist is a thioether substituted imidazoquinoline amine. In another alternative embodiment, the TLR8 agonist is a 6-, 7-, 8-, or 9-aryl or heteroaryl substituted imidazoquinoline amine.

In another alternative embodiment, the TLR8 agonist is an amide substituted tetrahydroimidazoquinoline amine. In another alternative embodiment, the TLR8 agonist is a sulfonamide substituted tetrahydroimidazoquinoline amine. In another alternative embodiment, the TLR8 agonist is a urea substituted tetrahydroimidazoquinoline amine. In another alternative embodiment, the TLR8 agonist is an aryl ether substituted tetrahydroimidazoquinoline amine. In another alternative embodiment, the TLR8 agonist is a heterocyclic ether substituted tetrahydroimidazoquinoline amine. In another alternative embodiment, the TLR8 agonist is an amido ether substituted tetrahydroimidazoquinoline amine. In another alternative embodiment, the TLR8 agonist is a sulfonamido ether substituted tetrahydroimidazoquinoline amine. In another alternative embodiment, the TLR8 agonist is a urea substituted tetrahydroimidazoquinoline ether. In another alternative embodiment, the TLR8 agonist is a thioether substituted tetrahydroimidazoquinoline amine.

In another alternative embodiment, the TLR8 agonist is an amide substituted imidazopyridine amines. In another alternative embodiment, the TLR8 agonist is a sulfonamide substituted imidazopyridine amine. In another alternative embodiment, the TLR8 agonist is a urea substituted imidazopyridine amine. In another alternative embodiment, the TLR8 agonist is an aryl ether substituted imidazopyridine amine. In another alternative embodiment, the TLR8 agonist is a heterocyclic ether substituted imidazopyridine amine. In another alternative embodiment, the TLR8 agonist is an amido ether substituted imidazopyridine amine. In another alternative embodiment, the TLR8 agonist is a sulfonamido ether substituted imidazopyridine amine. In another alternative embodiment, the TLR8 agonist is a urea substituted imidazopyridine ether. In another alternative embodiment, the TLR8 agonist is a thioether substituted imidazopyridine amine.

In another alternative embodiment, the TLR8 agonist is a 1,2-bridged imidazoquinoline amine. In another alternative embodiment, the TLR8 agonist is a 6,7-fused cycloalkylimidazopyridine amine.

In another alternative embodiment, the TLR8 agonist is an imidazonaphthyridine amine. In another alternative embodiment, the TLR8 agonist is a tetrahydroimidazonaphthyridine amine. In another alternative embodiment, the TLR8 agonist is an oxazoloquinoline amine. In another alternative embodiment, the TLR8 agonist is a thiazoloquinoline amine. In another alternative embodiment, the TLR8 agonist is an oxazolopyridine amine. In another alternative embodiment, the TLR8 agonist is a thiazolopyridine amine. In another alternative embodiment, the TLR8 agonist is an oxazolonaphthyridine amine. In another alternative embodiment, the TLR8 agonist is a thiazolonaphthyridine amine.

In yet another alternative embodiment, the TLR8 agonist is a 1H-imidazo dimer fused to a pyridine amine, quinoline amine, tetrahydroquinoline amine, naphthyridine amine, or a tetrahydronaphthyridine amine.

Suitable IRM compounds also include the purine derivatives, small heterocyclic compounds, amide derivatives, and oligonucleotide sequences described above. Alternatively, the IRM molecules employed in some methods according to the present invention may include compounds identified as TLR8 agonists by any suitable method of identifying a TLR8 agonist, including some of the methods according to the present invention.

In some embodiments, the TLR8-mediated cellular response may include production of at least one cytokine such as, for example, TNF-α, a Type I interferon, IFN-γ, IL-1, IL-6, IL-8, IL-10, IL-12, MIP-1, MCP-1, or any combination thereof. In other embodiments, the TLR-mediated cellular response may include activation of NF-κB. In still other embodiments, the TLR-mediated cellular response may include production of at least one co-stimulatory marker, an intercellular adhesion molecule, a maturation marker, or any combination thereof.

In certain embodiments, the TLR8-mediated cellular responses may be elicited in vitro. For example, TLR8-responsive cells may be either (a) engineered, or (b) collected from a subject, and then cultured in vitro. A TLR8 agonist may be administered to the in vitro cell culture, thereby eliciting a TLR-mediated cellular response. Alternatively, the TLR8-mediated cellular response may be elicited in vivo by administering a TLR8 agonist directly to a subject.

Suitable IRM-responsive cells include, but are not limited to, cells that naturally express TLR8, such as monocytes, macrophages, Langerhans cells, dendritic cells, Natural Killer cells, polymorphonuclear cells (e.g., neutrophils, basophils, or eosinophils), B lymphocytes, and cells derived from any of the foregoing. Alternatively, suitable IRM-responsive cells can include cells that do not naturally possess a readily detectable level of TLR8 expression, but have been genetically modified to provide a detectable level of TLR8 expression. For example, HEK293 cells may be transfected with a vector that includes an expressible TLR8 structural gene operably linked to one or more expression control sequences.

The activation of a TLR8 pathway of an organism may result in increased or decreased production of at least one cytokine or at least one co-stimulatory marker. Because the ability to control cytokine or co-stimulatory marker levels can be useful in the treatment of certain conditions, the present invention also provides methods of treating these conditions. It is possible that in certain embodiments, production of one or more cytokines or co-stimulatory markers will be induced, while the production of one or more other cytokines or co-stimulatory markers will be inhibited.

Therefore, the present invention provides a method of treating an organism having a condition treatable by modulating a TLR8-mediated cellular response. The method includes administering to the organism a TLR8 agonist in an amount effective to activate a TLR8-mediated cellular signaling pathway. The TLR8 agonist may be any IRM compound, such as those compounds described above, that can act as an agonist of TLR8.

The method may provide prophylactic treatment, therapeutic treatment, or both. As used herein, prophylactic treatment refers to treatment that is initiated prior to observation of symptoms and/or a suspected exposure to a causative agent of the condition (e.g., a pathogen or carcinogen). Generally, prophylactic treatment may reduce (a) the likelihood that a subject that receives the treatment develops the condition and/or (b) the duration and/or severity of symptoms in the event the subject develops the condition. As used herein, therapeutic treatment refers to treatment initiated after observation of symptoms and/or a suspected exposure to a causative agent of the condition. Generally, therapeutic treatment may reduce the severity and/or duration of symptoms associated with the condition.

Whether for prophylaxis or therapeutic treatment of a disease, and whether for effecting innate or acquired immunity, the TLR8 agonist may be administered alone or in combination with one or more active components as in, for example, a vaccine adjuvant. When administered with other components, the TLR8 agonist and other component or components may be administered separately; together but independently such as in a solution; or together and associated with one another such as (a) covalently linked or (b) non-covalently associated, e.g., in a colloidal suspension.

Activation of a TLR8 pathway also may be useful for treating a variety of disorders that are responsive to cytokines. Agents that activate the TLR8 pathway are expected to be particularly useful in the treatment of diseases or conditions treatable through a $T_H1$ immune response (e.g., viral diseases, certain bacterial diseases, and tumors).

Conditions for which TLR8 agonists may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, pneumocystis camii pneumonia, leishmaniasis, cryptosporidiosis, toxoplasmosis, and trypanosome infection; and (d) neoplastic diseases, such as intraepithelial neoplasias; cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers; and (e) $T_H2$-mediated, atopic, and autoimmune diseases, such as atopic dermatitis or eczema, eosinophilia, asthma, allergy, allergic rhinitis, systemic lupus erythematosus, essential thrombocythaemia, multiple sclerosis, Ommen's syndrome, discoid lupus, alopecia areata, inhibition of keloid formation and other types of scarring, and enhancing would healing, including chronic wounds.

TLR8 agonists also may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

TLR8 agonists may also be particularly helpful in individuals having compromised immune function. For example, TLR8 agonists may be used for treating the opportunistic infections and tumors that occur after suppression of cell mediated immunity in, for example, transplant patients, cancer patients and HIV patients.

An amount of a TLR8 agonist effective to activate a TLR8-mediated cellular signaling pathway is an amount sufficient to cause one or more cell types, such as monocytes, macrophages, dendritic cells and B-cells to produce a TLR8-mediated cellular response such as any one or more of the TLR8-mediated cellular responses described above. The precise amount of TLR8-agonist to induce such as response may vary according to factors known in the art but is expected to be a dose of about 100 ng/kg to about 50 mg/kg, preferably about 10 µg/kg to about 5 mg/kg.

In some embodiments, the TLR8 agonist can be a known IRM compound including the small organic IRM molecules described above, or the purine derivatives, small heterocyclic compounds, amide derivatives, and oligonucleotide sequences described above. Alternatively, the TLR8 agonists employed in some embodiments of the present invention may include compounds identified as TLR8 agonists by any suitable method of identifying a TLR8 agonist, including some of the methods according to the present invention.

The TLR8 agonist may be provided in any formulation suitable for administration to a subject. Suitable types of formulations are described, for example, in U.S. Pat. No. 5,736,553; U.S. Pat. No. 5,238,944; U.S. Pat. No. 5,939,090; U.S. Pat. No. 6,365,166; U.S. Pat. No. 6,245,776; U.S. Pat. No. 6,486,186; European Patent No. EP 0 394 026; and U.S. Patent Publication No. 2003/0199538. The TLR8 agonist may be provided in any suitable form including but not limited to a solution, a suspension, an emulsion, or any form of mixture. The TLR8 agonist may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including but not limited to adjuvants, skin penetration enhancers, colorants, fragrances, flavorings, moisturizers, thickeners, and the like.

A formulation containing one or more components of the combination may be administered in any suitable manner such as, for example, non-parenterally or parenterally. As used herein, non-parenterally refers to administration through the digestive tract, including by oral ingestion. Parenterally refers to administration other than through the digestive tract such as, for example, intravenously, intramuscularly, transdermally, subcutaneously, transmucosally (e.g., by inhalation), or topically.

In some embodiments, the methods of the present invention include administering a TLR8 agonist to a subject in a formulation of, for example, from about 0.0001% to about 10% (unless otherwise indicated, all percentages provided herein are weight/weight with respect to the total formulation) to the subject, although in some embodiments the TLR8 agonist may be administered using a formulation that provides the TLR8 agonist in a concentration outside of this range. In certain embodiments, the method includes administering to a subject a formulation that includes from about 0.01% to about 1% TLR8 agonist, for example, a formulation that includes from about 0.1% to about 0.5% TLR8 agonist.

An amount of a TLR8 agonist effective for treating a condition is an amount sufficient to provide the desired therapeutic or prophylactic benefit. The precise amount of TLR8 agonist for treating a condition will vary according to factors known in the art including but not limited to the condition, the physical and chemical nature of TLR8 agonist, the nature of the carrier, the intended dosing regimen, the state of the subject's immune system (e.g., suppressed, compromised, stimulated), the method of administering the TLR8 agonist, and the species to which the formulation is being administered. Accordingly, it is not practical to set forth generally the amount that constitutes an amount of TLR8 agonist effective for treating a condition for all possible applications. Those of ordinary skill in the art, however, can readily determine the appropriate amount with due consideration of such factors.

In some embodiments, the methods of the present invention include administering sufficient TLR8 agonist to provide a dose of, for example, from about 100 ng/kg to about 50 mg/kg to the subject, although in some embodiments the methods may be performed by administering the TLR8 agonist in concentrations outside this range. In some of these embodiments, the method includes administering sufficient TLR8 agonist to provide a dose of from about 10 µg/kg to about 5 mg/kg to the subject, for example, a dose of from about 100 µg/kg to about 1 mg/kg.

The dosing regimen may depend at least in part on many factors known in the art including but not limited to the condition, the physical and chemical nature of the TLR8 agonist, the nature of the carrier, the amount of TLR8 agonist being administered, the state of the subject's immune system (e.g., suppressed, compromised, stimulated), the method of administering the TLR8 agonist, and the species to which the formulation is being administered. Accordingly it is not practical to set forth generally the dosing regimen effective for treating a condition for all possible applications. Those of ordinary skill in the art, however, can readily determine the appropriate amount with due consideration of such factors.

In some embodiments of the invention, the TLR8 agonist may be administered, for example, from a single dose to multiple doses per day, although in some embodiments the methods of the present invention may be performed by administering the TLR8 agonist at a frequency outside this range. In certain embodiments, the TLR8 agonist may be administered from about once per week to about three times per day such as, for example, administering the TLR8 agonist once per day.

The organism treated for a condition may be a plant or animal, particularly a vertebrate. Preferably the organism treated for the disorder is a mammal, such as, but not limited to, human, rodent, dog, cat, pig, sheep, goat, or cow.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

Compounds

The compounds used in the following Examples and citations for methods for synthesizing each compound are provided in Table 1.

TABLE 1

| Compound | Chemical Name | Citation |
| --- | --- | --- |
| IRM1 | 4-amino-2-ethoxymethyl-α,α-dimethyl-6,7,8,9-tetrahydro-1H-imidazo[4,5-c]quinoline-1-ethanol | U.S. Pat. No. 5,352,784 Example 91 |
| IRM2 | 4-amino-α,α-dimethyl-2-methoxyethyl-1H-imidazo[4,5-c]quinoline-1-ethanol | U.S. Pat. No. 5,389,640 Example 111 |
| IRM3 | 2-propylthiazolo[4,5-c]quinolin-4-amine | U.S. Pat. No. 6,110,929 Example 12 |
| IRM4 | 1-{2-[3-(benzyloxy)propoxy]ethyl}-2-(ethoxymethyl)-1H-imidazo[4,5-c]quinolin-4-amine | WO 02/46819 Example 21 |
| IRM5 | N-[4-(4-amino-2-butyl-1H-imidazo[4,5-c][1,5]naphthyridin-1-yl)butyl]-n'-butylurea | U.S. Pat. No. 6,194,425 Example 49 |
| IRM6 | $N^1$-[2-(4-amino-2-butyl-1H-imidazo[4,5-c][1,5]naphthyridin-1-yl)ethyl]-2-amino-4-methylpentanamide | U.S. Pat. No. 6,194,425 Example 102 |
| IRM7 | $N^1$-[4-(4-amino-1H-imidazo[4,5-c]quinolin-1-yl)butyl]-2-phenoxybenzamide | U.S. Pat. No. 6,451,810 Example 14 |
| IRM8 | 1-(2-{[3-(4-pyridyl)-2-propynyl]oxy}ethyl)-1H-imidazo[4,5-c]quinolin-4-amine bis(trifluoroacetate) | WO 02/46193 Example 18 |
| IRM9 | N-[2-(4-amino-2-butyl-1H-imidazo[4,5-c]quinolin-1-yl)ethyl]methanesulfonamide | U.S. Pat. No. 6,331,539 Example 34*** |
| IRM10 | N-(2-{2-[4-amino-2-(2-methoxyethyl)-1H-imidazo[4,5-c]quinolin-1-yl]ethoxy}ethyl)-n'-phenylurea | U.S. Pat. No. 6,656,938 Example 1 |
| IRM11 | 1-(2-amino-2-methylpropyl)-2-(ethoxymethyl)-1H-imidazo[4,5-c]quinolin-4-amine | U.S. Pat. No. 6,069,149# |
| IRM12 | 1-{4-[(3,5-dichlorophenyl)sulfonyl]butyl}-2-ethyl-1H-imidazo[4,5-c]quinolin-4-amine | U.S. Pat. No. 6,667,312 Example 46 |
| IRM13 | N-(2-{2-[4-amino-2-(ethoxymethyl)-1H-imidazo[4,5-c]quinolin-1-yl]ethoxy}ethyl)-n'-cyclohexylurea | U.S. Pat. No. 6,660,735# |
| IRM14 | N-{3-[4-amino-2-(ethoxymethyl)-1H-imidazo[4,5-c]quinolin-1-yl]propyl}-n'-(3-cyanophenyl)thiourea | WO 00/76518# |
| IRM15 | N-[3-(4-amino-2-butyl-1H-imidazo[4,5-c]quinolin-1-yl)-2,2-dimethylpropyl]benzamide | U.S. Pat. No. 4,651,810# |
| IRM16 | N-[4-(4-amino-2-ethyl-1H-imidazo[4,5-c]quinolin-1-yl)butyl]methanesulfonamide | U.S. Pat. No. 6,331,539# |
| IRM17 | N-[4-(4-amino-2-butyl-1H-imidazo[4,5-c][1,5]naphthyridin-1-yl)butyl]-n'-cyclohexylurea | U.S. Pat. No. 6,194,425 Example 48 |
| IRM18 | N-{2-[4-amino-2-(ethoxymethyl)-1H-imidazo[4,5-c]quinolin-1-yl]-1,1-dimethylethyl}methanesulfonamide | U.S. Pat. No. 6,677,349 Example 268 |
| IRM19 | 2-butyl-1-[2-(isopropylsulfonyl)ethyl]-1H-imidazo[4,5-c]quinolin-4-amine | U.S. Pat. No. 6,667,312 Example 56 |
| IRM20 | N-{2-[4-amino-2-(ethoxymethyl)-1H-imidazo[4,5-c]quinolin-1-yl]-1,1-dimethylethyl}-n'-cyclohexylurea | U.S. Pat. No. 6,573,273# |
| IRM21 | N-{2-[4-amino-2-(ethoxymethyl)-1H-imidazo[4,5-c]quinolin-1-yl]-1,1-dimethylethyl}cyclohexanecarboxamide | U.S. Pat. No. 2003/0144283# |
| IRM22 | N-{2-[4-amino-2-(ethoxymethyl)-6,7,8,9-tetrahydro-1H-imidazo[4,5-c]quinolin-1-yl]-1,1-dimethylethyl}methanesulfonamide | U.S. Pat. No. 6,677,349# |
| IRM23 | N-[2-(4-amino-2-propyl-1H-imidazo[4,5-c]quinolin-1-yl)-1,1-dimethylethyl]methanesulfonamide | U.S. Pat. No. 6,677,349# |
| IRM24 | 2-ethoxymethyl-$N^1$-isopropyl-1H-imidazo[4,5-c]quinoline-1,4-diamine | U.S. Ser. No. 60/453128 Example 5 |

TABLE 1-continued

| Compound | Chemical Name | Citation |
|---|---|---|
| IRM25 | N¹-[2-(4-amino-2-butyl-1H-imidazo[4,5-c]quinolin-1-yl)ethyl]-1-propanesulfonamide | U.S. Pat. No. 6,331,539 Example 17 |
| IRM26 | 2-butyl-1-[2-(propylsulfonyl)ethyl]-1H-imidazo[4,5-c]quinolin-4-amine | U.S. Pat. No. 6,667,312 Example 62 |
| IRM27 | N-{2-[4-amino-2-(2-methoxyethyl)-1H-imidazo[4,5-c]quinolin-1-yl]-1,1-dimethylethyl}methanesulfonamide | U.S. Pat. No. 6,677,349[#] |
| IRM28 | N-{2-[4-amino-2-(2-methoxyethyl)-6,7,8,9-tetrahydro-1H-imidazo[4,5-c]quinolin-1-yl]-1,1-dimethylethyl}methanesulfonamide | U.S. Pat. No. 6,331,539[#] |
| IRM29 | N-[2-(4-amino-2-butyl-6,7,8,9-tetrahydro-1H-imidazo[4,5-c]quinolin-1-yl)-1,1-dimethylethyl]methanesulfonamide | U.S. Pat. No. 6,677,349[#] |
| IRM30 | N-[2-(4-amino-2-ethyl-6,7,8,9-tetrahydro-1H-imidazo[4,5-c]quinolin-1-yl)-1,1-dimethylethyl]methanesulfonamide | U.S. Pat. No. 6,677,349[#] |
| IRM31 | 1-[4-amino-2-(methoxyethyl)-7-(pyridin-3-yl)-1H-imidazo[4,5-c]quinolin-1-yl]-2-methylpropan-2-ol | U.S. Ser. No. 10/739787 Example 138 |
| IRM32 | N-{2-[4-amino-2-(ethoxymethyl)-6,7,8,9-tetrahydro-1H-imidazo[4,5-c]quinolin-1-yl]-1,1-dimethylethyl}-n'-cyclohexylurea | U.S. Pat. No. 6,573,273[#] |
| IRM33 | N-(2-{2-[4-amino-2-(ethoxymethyl)-1H-imidazo[4,5-c]quinolin-1-yl]ethoxy}ethyl)-n'-phenylurea | U.S. Pat. No. 6,660,735 Example 53 |
| IRM34 | 1-[2-(methylsulfonyl)ethyl]-2-propyl-1H-imidazo[4,5-c]quinolin-4-amine | U.S. Pat. No. 6,667,312 Example 36 |
| IRM35 | N-[4-(4-amino-2-propyl-1H-imidazo[4,5-c]quinolin-1-yl)butyl]-n'-phenylurea | U.S. Pat. No. 6,573,273 Example 160 |
| IRM36 | N-[2-(2-butyl-4-methyl-1H-imidazo[4,5-c]quinolin-1-yl)ethyl]thiophene-2-sulfonamide | U.S. Pat. No. 6,331,593 Example 19* |
| IRM37 | N-{4-[4-amino-2-(2-methoxyethyl)-1H-imidazo[4,5-c]quinolin-1-yl]butyl}quinoline-3-carboxamide | U.S. Pat. No. 2003/0144283 Example 182 |
| IRM38 | N-{4-[4-amino-2-(2-methoxyethyl)-1H-imidazo[4,5-c]quinolin-1-yl]butyl}quinoxaline-2-carboxamide | U.S. Pat. No. 2003/0144283 Example 183 |
| IRM39 | N-[3-(4-amino-2-butyl-1H-imidazo[4,5-c]quinolin-1-yl)propyl]morpholine-4-carboxamide | U.S. Pat. No. 6,573,273 Example 151 |
| IRM40 | 2-butyl-1-[3-(methylsulfonyl)propyl]-1H-imidazo[4,5-c]quinolin-4-amine | U.S. Pat. No. 6,664,264 Example 19 |
| IRM41 | N-(2-{2-[4-amino-2-(methoxyethyl)-6,7,8,9-tetrahydro-1H-imidazo[4,5-c]quinolin-1-yl]ethoxy}ethyl)-n'-phenylurea | U.S. Pat. No. 6,656,938 Example 2 |
| IRM42 | 2-butyl-1-[2-(ethylsulfonyl)ethyl]-1H-imidazo[4,5-c]quinolin-4-amine | U.S. Pat. No. 6,667,312 Example 66 |
| IRM43 | N-{2-[4-amino-2-(ethoxymethyl)-1H-imidazo[4,5-c]quinolin-1-yl]-1,1-dimethylethyl}-2-ethoxyacetamide | U.S. Pat. No. 2003/0144283 Example 209 |
| IRM44 | 2-ethyl-1-[2-(methylsulfonyl)ethyl]-1H-imidazo[4,5-c]quinolin-4-amine | U.S. Pat. No. 6,667,312 Example 35 |
| IRM45 | 2-butyl-1-[2-(methylsulfonyl)ethyl]-1H-imidazo[4,5-c]quinolin-4-amine | U.S. Pat. No. 6,667,312 Example 67 |
| IRM46 | N-[3-(4-amino-2-butyl-1H-imidazo[4,5-c]quinolin-1-yl)-2,2-dimethylpropyl]morpholine-4-carboxamide | U.S. Pat. No. 6,573,273[#] |
| IRM47 | N-{2-[4-amino-2-(ethoxymethyl)-1H-imidazo[4,5-c]quinolin-1-yl]-1,1-dimethylethyl}-n'-isopropylurea | U.S. Pat. No. 6,573,273[#] |
| IRM48 | 2-ethoxymethyl-7-phenyl-1-(piperidin-4-ylmethyl)-1H-imidazo[4,5-c]quinolin-4-amine | U.S. Ser. No. 10/739787 Example 192 |
| IRM49 | 1-[4-amino-7-(5-hydroxymethylpyridin-3-yl)-2-(2-methoxyethyl)-1H-imidazo[4,5-c]quinolin-1-yl]-2-methylpropan-2-ol | U.S. Ser. No. 10/739787 Example 141 |
| IRM50 | N-{3-[4-amino-1-(2-hydroxy-2-methylpropyl)-2-(methoxyethyl)-1H-imidazo[4,5-c]quinolin-7-yl]phenyl}methanesulfonamide | U.S. Ser. No. 10/739787 Example 139 |
| IRM51 | 1-[4-amino-2-(ethoxymethyl)-7-(pyridin-3-yl)-1H-imidazo[4,5-c]quinolin-1-yl]-2-methylpropan-2-ol | U.S. Ser. No. 10/739787 Example 126 |
| IRM52 | 1-{4-amino-2-(ethoxymethyl)-7-[5-(hydroxymethyl)pyridin-3-yl]-1H-imidazo[4,5-c]quinolin-1-yl}-2-methylpropan-2-ol | U.S. Ser. No. 10/739787 Example 133 |
| IRM53 | 1-[(2,2-dimethyl-1,3-dioxolan-4-yl)methyl]-2-(ethoxymethyl)-7-(4-hydroxymethylphenyl)-1H-imidazo[4,5-c]quinolin-4-amine | U.S. Ser. No. 10/739787 Example 160 |
| IRM54 | 1-[2-(4-amino-2-ethoxymethyl-1H-imidazo[4,5-c]quinolin-1-yl)-1,1-dimethylethyl]-3-cyclopentylurea | U.S. Pat. No. 6,573,273[#] |

TABLE 1-continued

| Compound | Chemical Name | Citation |
|---|---|---|
| IRM55 | 1-[2-(4-amino-2-ethoxymethyl-1H-imidazo[4,5-c]quinolin-1-yl)-1,1-dimethylethyl]-3-propylurea | U.S. Pat. No. 6,573,273[#] |
| IRM56 | 1-[4-amino-2-ethoxymethyl-7-(pyridin-4-yl)-1H-imidazo[4,5-c]quinolin-1-yl]-2-methylpropan-2-ol | U.S. Ser. No. 10/739787 Example 127 |
| IRM57 | 3-[4-amino-2-(ethoxymethyl)-7-(pyridin-3-yl)-1H-imidazo[4,5-c]quinolin-1-yl]propane-1,2-diol | U.S. Ser. No. 10/739787 Example 162 |
| IRM58 | {3-[4-amino-2-ethoxymethyl-1-(2-hydroxy-2-methylpropyl)-1H-imidazo[4,5-c]quinolin-7-yl]phenyl}pyrrolidin-1-ylmethanone | U.S. Ser. No. 10/739787 Example 129 |
| IRM59 | 1-[4-amino-2-ethyl-7-(pyridin-4-yl)-1H-imidazo[4,5-c]quinolin-1-yl]-2-methylpropan-2-ol | U.S. Ser. No. 10/739787 Example 143 |
| IRM60 | 2-ethoxymethyl-$N^1$-isopropyl-6,7,8,9-tetrahydro-1H-imidazo[4,5-c]quinoline-1,4-diamine | U.S. Ser. No. 60/532191 Example 11 |
| IRM61 | 4-[4-amino-2-ethoxymethyl-1-(2-hydroxy-2-methylpropyl)-1H-imidazo[4,5-c]quinolin-7-yl]-N-methoxy-N-methylbenzamide | U.S. Ser. No. 10/739787 Example 132 |

***Example 34 shows synthesis of trifluoroacetate salts, which may be converted to the free base using conventional methods.
[#]This compound is not specifically exemplified but can be readily prepared using the synthetic methods disclosed in the cited reference.

Cells

HEK293 cells—immortalized human embryonic kidney cells, available from American Type Culture Collection, Manassas, Va., ATCC No. CRL-1573.

Cell Culture Media/Buffers

Complete RPMI was prepared by mixing RPMI 1640 with 25 mM HEPES, 1 mM sodium pyruvate, 0.1 mM non-essential amino acids, and 1 mM L-glutamine (Celox Laboratories, Inc., Minneapolis, Minn.) supplemented with 10% heat inactivated fetal calf serum (FCS) (Hyclone Laboratories, Inc., Logan, Utah) and 1% penicillin/streptomycin (Sigma Chemical Co., St. Louis, Mo.).

IGEN PBS Buffer was prepared from Dulbecco's Phosphate Buffered Saline without calcium or magnesium (DPBS, Biosource International, Camarillo, Calif.), with 0.5% bovine serum albumin (BSA), 0.2% Tween, and 0.05% azide.

Example 1

Expression of TLR8 in HEK293 Cells

HEK293 cells were cultured in 90% Minimum Essential Medium (MEM) with 2 mM L-glutamine and Earle's Balanced Salt Solution (Invitrogen Corp., Rockville, Md.) adjusted to contain 1.5 g/L sodium bicarbonate, 0.1 mM non-essential amino acids, and 1.0 mM sodium pyruvate; 10% heat-inactivated fetal calf serum. The cells were incubated at 37° C., 8% $CO_2$.

Twenty-four hours before transfection, HEK293 cells were adhered to a 10 cm dish (Corning 430167, Corning Inc., Corning, N.Y.) at 37° C., 8% $CO_2$. The cells were co-transfected with (1) pIRES (BD Biosciences Clontech, Palo Alto, Calif.) either (a) unmodified (HEK293-vector) or (b) containing human TLR8 (HEK293-TLR8), and (2) NFkB-luc reporter (Stratagene, La Jolla, Calif.) in a 10:1 ratio with Fugene 6 transfection reagent (Roche Diagnostics Corp., Indianapolis, Ind.) following the manufacturer's instructions. The plates were incubated for 24 hours following transfection and then selected in G-418 (400 μg/mL) for two weeks. The G-418-resistant cells containing either the TLR8 or empty vector were expanded in HEK293 media supplemented with G-418 for stimulation experiments.

The transfected cells were plated in white opaque 96 well plates (Costar 3917, Corning Inc., Corning, N.Y.) at a concentration of $5 \times 10^4$ cells per well in 100 μL of HEK293 media and incubated at 37° C., 8% $CO_2$ for 4 hours. The cells were stimulated with 1 μL of IRM compounds at 1 mM in DMSO (final IRM concentration of 10 μM) or 1 μL DMSO as a control. The plates were then incubated an additional 16 hours at 37° C., 5% $CO_2$. Luminescence was measured on an LMAX luminometer (Molecular Devices Corp., Sunnyvale, Calif.).

TABLE 2

| | Fold Increase Over DMSO Control | | |
|---|---|---|---|
| Stimulus | HEK293-vector | HEK293-TLR8 | HEK293-TLR8 HEK293-vector |
| IRM 1 | 0.85 | 8.64 | 10.2 |
| IRM 2 | 1.16 | 10.18 | 8.8 |
| IRM 3 | 0.75 | 10.11 | 13.5 |
| IRM 4 | 0.41 | 2.64 | 6.4 |
| IRM 5 | 0.84 | 2.13 | 2.5 |
| IRM 6 | 1.19 | 9.24 | 7.8 |
| IRM 7 | 1.02 | 10.69 | 10.5 |
| IRM 8 | 1.18 | 2.38 | 2.0 |
| IRM 9 | 0.77 | 8.64 | 11.2 |
| IRM 10 | 1.08 | 7.25 | 6.7 |
| IRM 11 | 1.47 | 3.14 | 2.1 |
| IRM 12 | 1.16 | 6.04 | 5.2 |
| IRM 13 | 0.99 | 2.33 | 2.3 |
| IRM 14 | 1.26 | 10.00 | 7.9 |
| IRM 15 | 0.78 | 2.14 | 2.7 |
| DMSO | 1.00 | 1.00 | 1.0 |

Example 2

Stimulation of Monocytes by TLR8 Agonists

Whole blood was collected in 60 mL syringes filled with 750 μL of 0.5 M EDTA, pH 8.0 (Gibco, Grand Island, N.Y.).

Blood was diluted 1:1 in Dulbecco's Phosphate Buffered Saline without calcium or magnesium (DPBS, Biosource International, Camarillo, Calif.) and overlayed with Histopaque-1077 (Sigma Chemical Co., St. Louis, Mo.). Cells were centrifuged at 2000 RPM for 30 minutes at 25° C. The buffy coat layer was isolated and washed three times with DPBS at 1350 RPM for 10 minutes at 25° C.

The monocytes were isolated from the PBMCs using the Miltenyi Microbead technology system (Miltenyi BioTec, Auburn, Calif.). PBMCs were resuspended in 4° C. separation buffer (PBS— pH 7.2, 0.5% BSA—2.5 μm, 2 mM 0.5M EDTA) at 60 μl per $10^7$ total cells. CD14+ microbeads (cat. no. 130-050-201, Miltenyi BioTec) and FcR Blocking Reagent (cat. no. 130-059-901, Miltenyi BioTec) were each added at 20 μL per $10^7$ total cells and incubated for 15 minutes at 4° C. The cells were centrifuged at 1350 RPM for 10 minutes at 25° C. and resuspended in 500 μL of separation buffer per $10^8$ total cells. The cells were then added to an LS+ column (cat. no. 130-042-401, Miltenyi BioTec) topped with a pre-separation filter (cat. no. 130-041-407, Miltenyi BioTec) and washed three times with separation buffer. The negative cells were allowed to pass through the column. The cells retained in the column were eluted with 5 mL of separation buffer into a sterile 15 mL polystyrene conical tube. The CD14+ cells were centrifuged at 1350 RPM for 10 minutes at 25° C. and resuspended in X-VIVO 20 (BioWhittaker, Walkersville, Md.) at $2\times10^6$ cells/mL.

Compounds, reconstituted in dimethyl sulfoxide (DMSO, sterile cell culture grade, Sigma Chemical Co., St. Louis, Mo.) were added at 2× their final concentration to a 96-well flat-bottom sterile tissue culture polystyrene plate (Benton Dickinson Labware, Franklin Lakes, N.J.) at 60 μM, and then serially diluted 1:3 to 0.02 μM. Cells were then added at 2× the final concentration (final cell concentration is $1\times10^6$ cells/mL). Negative controls using IRM 16, an IRM compound identified as one that does not activate TLR8, were added for reference. Plates were incubated for 16-24 hours at 37° C., 5% $CO_2$. After incubation, plates were centrifuged at 1000 RPM for 10 minutes at 25° C. Supernatants were transferred to a 0.75 mL sterile polypropylene Matrix box (Matrix, Hudson, N.Y.) and stored at −20° C. for future cytokine analysis.

IL-12 analysis was performed using IGEN analysis. More than two hours prior to performing the analysis, a 1:20 dilution of M-280 Streptavidin Dynabeads was prepared in IGEN buffer. Also, a 1 μg/mL solution of biotinylated IL-12 antibody (Cat. No. AHC7129, Biosource International, Camarillo, Calif.) in IGEN buffer was prepared. The 1:20 Dynabeads solution and the biotinylated antibody solution were mixed together and incubated 30 minutes at room temperature, then stored at 4° C. until the analysis was performed.

To perform the analysis, 50 μL of the Dynabeads/biotinylated antibody solution was added to each well of a 96-well plate. Next, 25 μL of 1 μg/mL solution of Ori-tagged IL-12 antibody (Cat. No. 8122, Biosource International, Camarillo, Calif.) in IGEN buffer was added to each well. 25 μL of sample was added to each well, each sample containing either a standard dilutions or an experimental sample.

The 96-well plate was tapped to mix the contents of each well, covered with plate sealer, and incubated at room temperature for 2.5 hours.

Following the incubation, 100 μL of IGEN PBS Buffer was added to each well for a total assay volume of 200 μL and read on the IGEN M-8 Analyzer (IGEN International, Inc., Gaithersburg, Md.) using the hIL-12 protocol.

TNF analysis was performed using IGEN analysis similar to that used for IL-12 analysis, except that (1) the biotinylated antibody solution was prepared with 2 μg/mL of biotinylated TNF antibody (Cat. No. AHC3419, Biosource International, Camarillo, Calif.) in IGEN buffer; (2) the Ori-tagged antibody was a TNF antibody (Cat. No. AHC3712, Biosource International, Camarillo, Calif.); and (3) the assay was read by the IGEN M-8 Analyzer using the hTNF protocol.

Figure 2:
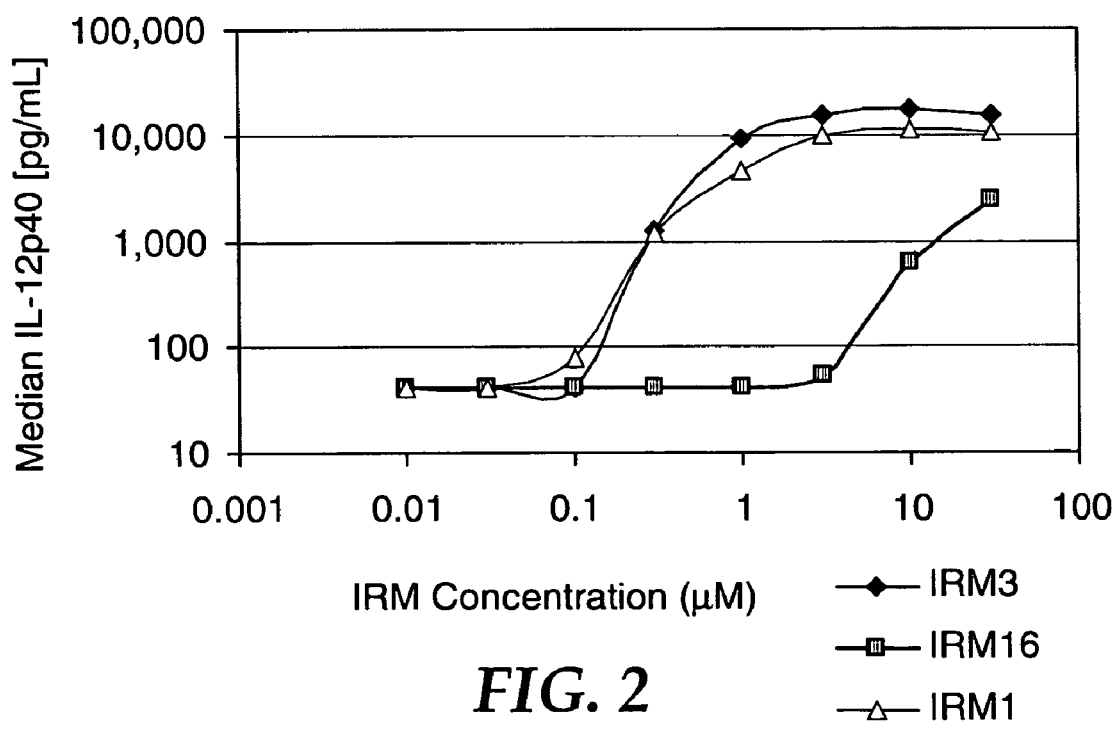
FIG. 2 is a line graph showing induction of IL-12 in human monocytes by TLR8 agonists.

Results are shown in FIGS. 1 and 2.

Example 3

Stimulation of Monocyte-Derive Dendritic Cells by TLR8 Agonists

Whole blood was collected in 60 mL syringes filled with 750 μL of 0.5M EDTA, pH 8.0 (Gibco, Grand Island, N.Y.). Blood was diluted 1:1 in Dulbecco's Phosphate Buffered Saline without calcium or magnesium (DPBS, Biosource International, Camarillo, Calif.) and overlayed with Histopaque-1077 (Sigma Chemical Co., St. Louis, Mo.). Cells were centrifuged at 2000 RPM for 30 minutes at 25° C. The buffy coat layer was isolated and washed three times with DPBS at 1350 RPM for 10 minutes at 25° C.

The monocytes were isolated from the PBMCs using the Miltenyi Microbead technology system (Miltenyi BioTec, Auburn, Calif.). PBMCs were resuspended in 4° C. separation buffer (PBS— pH 7.2, 0.5% BSA-2.5 gm, 2 mM 0.5M EDTA) at 60 μl per $10^7$ total cells. CD14+ microbeads (cat. no. 130-050-201, Miltenyi BioTec) and FcR Blocking Reagent (cat. no. 130-059-901, Miltenyi BioTec) were each added at 20 μl per $10^7$ total cells and incubated for 15 minutes at 4° C. The cells were centrifuged at 1350 RPM for 10 minutes at 25° C. and resuspended in 500 μL of separation buffer per $10^8$ total cells. The cells were then added to an LS+ columns (cat. no. 130-042-401, Miltenyi BioTec) topped with a pre-separation filter (cat. no. 130-041-407, Miltenyi BioTec) and washed three times with separation buffer. The negative cells were allowed to pass through the column. The cells left in the column were eluted with 5 mL of separation buffer into a sterile 15 mL polystyrene conical tube. The CD14+ cells were centrifuged at 1350 RPM for 10 minutes at 25° C. and resuspended in cRPMI (RPMI 1640, Celox Laboratories, Inc, St. Paul, Minn.; 10% heat-inactivated FBS, Atlas, Ft. Collins, Colo.; and 0.1% Gentamicin, Sigma Chemical Co.). The CD14+ cells were plated at $1\times10^6$ cells/mL into an appropriate volume tissue culture flask (Benton Dickinson Labware, Franklin Lakes, N.J.) with cRPMI, rIL-4 (Biosource International), rGM-CSF (Biosource International), and TGFβ (R&D Systems, Inc., Minneapolis, Minn.) for 5-7 days at 37° C., 5% $CO_2$.

Cells were removed from the flask, centrifuged at 1350 RPM for 10 minutes at 25° C., and resuspended in cRPMI at $2\times10^6$ cells/mL. Compounds, reconstituted in dimethyl sulfoxide (DMSO, sterile cell culture grade, Sigma Chemical Co., St. Louis, Mo.) were added at 2× their final concentration to a 96-well flat-bottom sterile tissue culture polystyrene plate (Benton Dickinson Labware, Franklin Lakes, N.J.) at 20 μM and serially diluted 1:3 to 0.6 μM. Cells were then added at 2× the final concentration (final cell concentration is $1\times10^6$ cells/mL). Negative controls using IRM 16, an IRM compound identified as one that does not activate TLR8, were added for reference. Plates were incubated for 16-24 hours at 37° C., 5% $CO_2$. After incubation, plates were centrifuged at 1000 RPM for 10 minutes at 25° C. Supernatants were transferred to a 0.75 mL sterile polypropylene Matrix box (Matrix, Hudson, N.Y.) and stored at −20° C. for future cytokine analysis.

Figure 3:
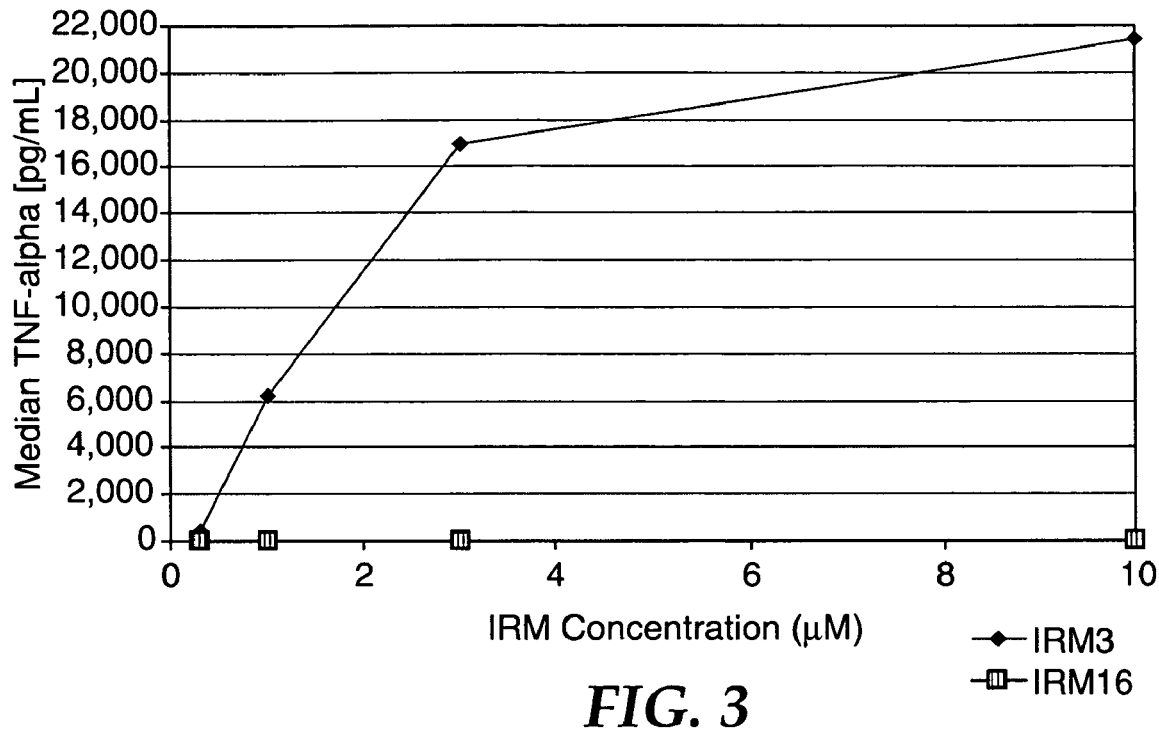
FIG. 3 is a line graph showing induction of TNF-α in human monocyte-derived dendritic cells by a TLR8 agonist.
Figure 4:
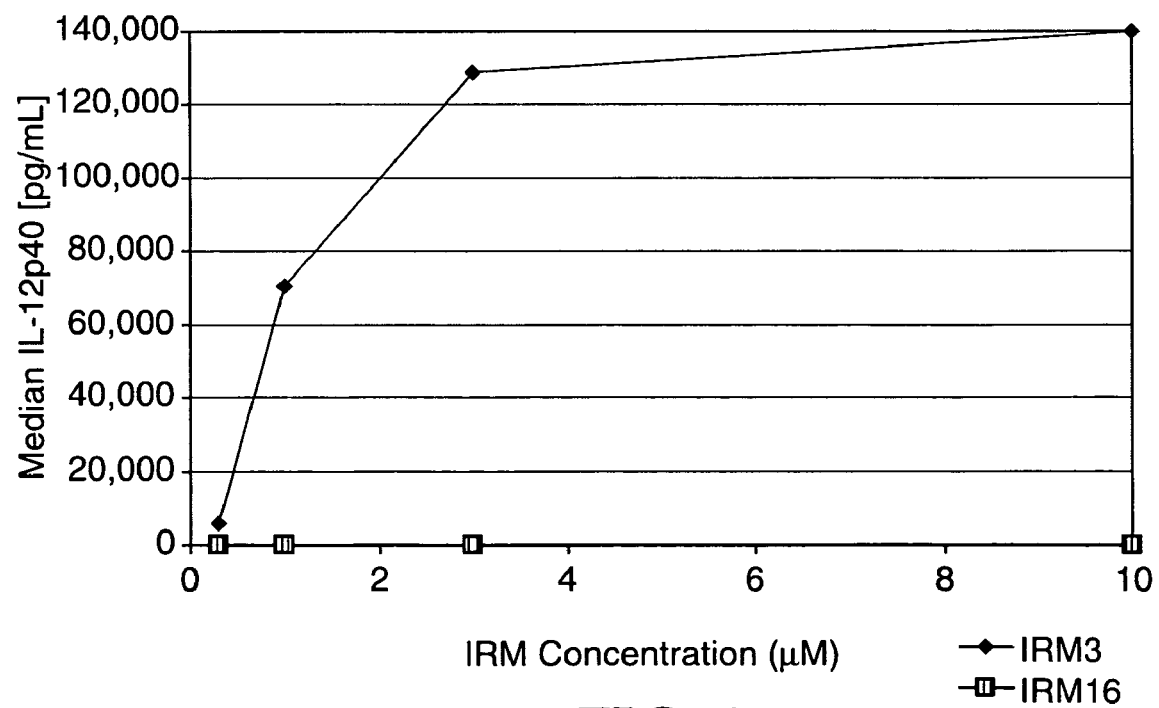
FIG. 4 is a line graph showing induction of IL-12 in human monocyte-derived dendritic cells by a TLR8 agonist.

Cytokine analysis was performed as described in Example 2. Results are shown in FIGS. 3 and 4.

Example 4

Stimulation of Macrophages by TLR8 Agonists

Whole blood was collected in 60 mL syringes filled with 750 μL 0.5M pH 8.0 EDTA (Gibco, Grand Island, N.Y.). Blood was diluted 1:1 in Dulbecco's Phosphate Buffered Saline without calcium or magnesium (DPBS, Biosource International, Camarillo, Calif.) and overlayed with Histopaque-1077 (Sigma Chemical Co., St. Louis, Mo.). Cells were centrifuged at 2000 RPM for 30 minutes at 25° C. The buffy coat layer was isolated and washed three times with DPBS at 1350 RPM for 10 minutes at 25° C.

The monocytes were isolated from the PBMCs using the Miltenyi Microbead technology system (Miltenyi BioTec, Auburn, Calif.). PBMCs were resuspended in 4° C. separation buffer (PBS— pH 7.2, 0.5% BSA—2.5 gm, 2 mM 0.5M EDTA) at 60 μl per $10^7$ total cells. CD14+ microbeads (cat. no. 130-050-201, Miltenyi BioTec) and FcR Blocking Reagent (cat. no. 130-059-901, Miltenyi BioTec) were each added at 20 μl per $10^7$ total cells and incubated for 15 minutes at 4° C. The cells were centrifuged at 1350 RPM for 10 minutes at 25° C. and resuspended in 500 μL of separation buffer per $10^8$ total cells. The cells were then added to an LS+ columns (cat. no. 130-042-401, Miltenyi BioTec) topped with a pre-separation filter (cat. no. 130-041-407, Miltenyi BioTec) and washed three times with separation buffer. The negative cells were allowed to pass through the column. The cells left in the column were eluted with 5 mL of separation buffer into a sterile 15 mL polystyrene conical tube. The CD14+ cells were centrifuged at 1350 RPM for 10 minutes at 25° C. and resuspended in cRPMI (RPMI 1640, Celox Laboratories, Inc, St. Paul, Minn.; 10% heat-inactivated FBS, Atlas, Ft. Collins, Colo.; and 0.1% Gentamicin, Sigma Chemical Co.). The CD14+ cells were plated at $1 \times 10^6$ cells/mL into an appropriate volume tissue culture flask (Benton Dickinson Labware, Franklin Lakes, N.J.) with cRPMI and GM-CSF (R&D Systems, Inc.) for 5-7 days at 37° C., 5% $CO_2$.

Cells were removed from the flask, centrifuged at 1350 RPM for 10 minutes at 25° C., and resuspended in cRPMI at $2 \times 10^6$ cells/mL. Compounds, reconstituted in dimethyl sulfoxide (DMSO, sterile cell culture grade, Sigma Chemical Co., St. Louis, Mo.) were added at 2× their final concentration to a 96-well flat-bottom sterile tissue culture polystyrene plate (Benton Dickinson Labware, Franklin Lakes, N.J.) at 20 μM and serially diluted 1:3 to 0.6 μM. Cells were then added at 2× the final concentration (final cell concentration is $1 \times 10^6$ cells/mL). Negative controls using IRM 16, an IRM compound identified as one that does not activate TLR8, were added for reference. Plates were incubated for 16-24 hours at 37° C., 5% $CO_2$. After incubation, plates were centrifuged at 1000 RPM for 10 minutes at 25° C. Supernatants were transferred to a 0.75 mL sterile polypropylene Matrix box (Matrix, Hudson, N.Y.) and stored at −20° C. for future cytokine analysis.

Figure 5:
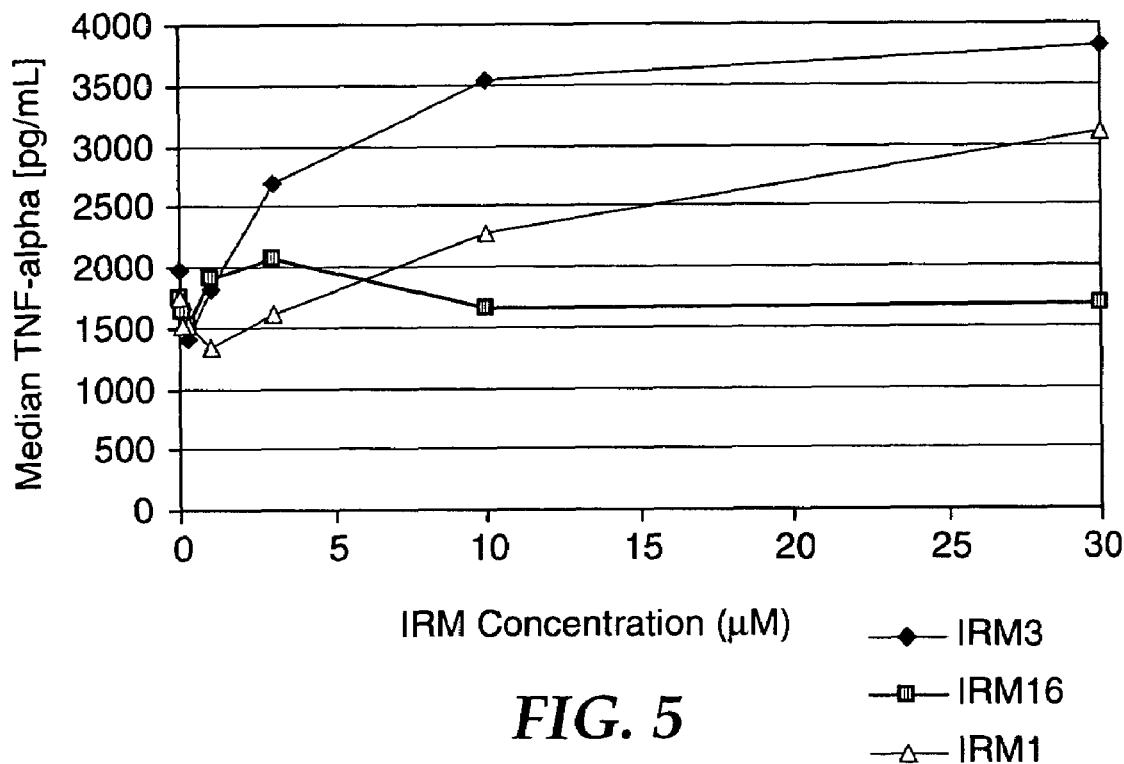
FIG. 5 is a line graph showing induction of TNF-α in human macrophages by TLR8 agonists.
Figure 6:
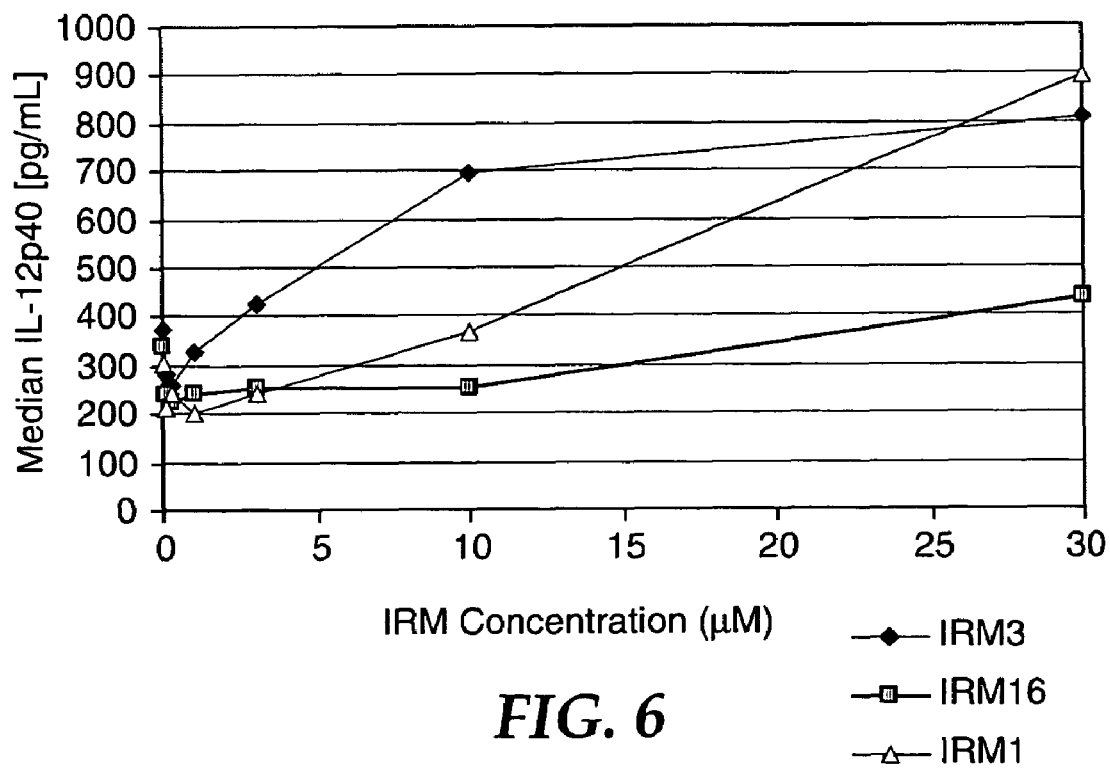
FIG. 6 is a line graph showing induction of IL-12 in human macrophages by TLR8 agonists.
Figure 7:
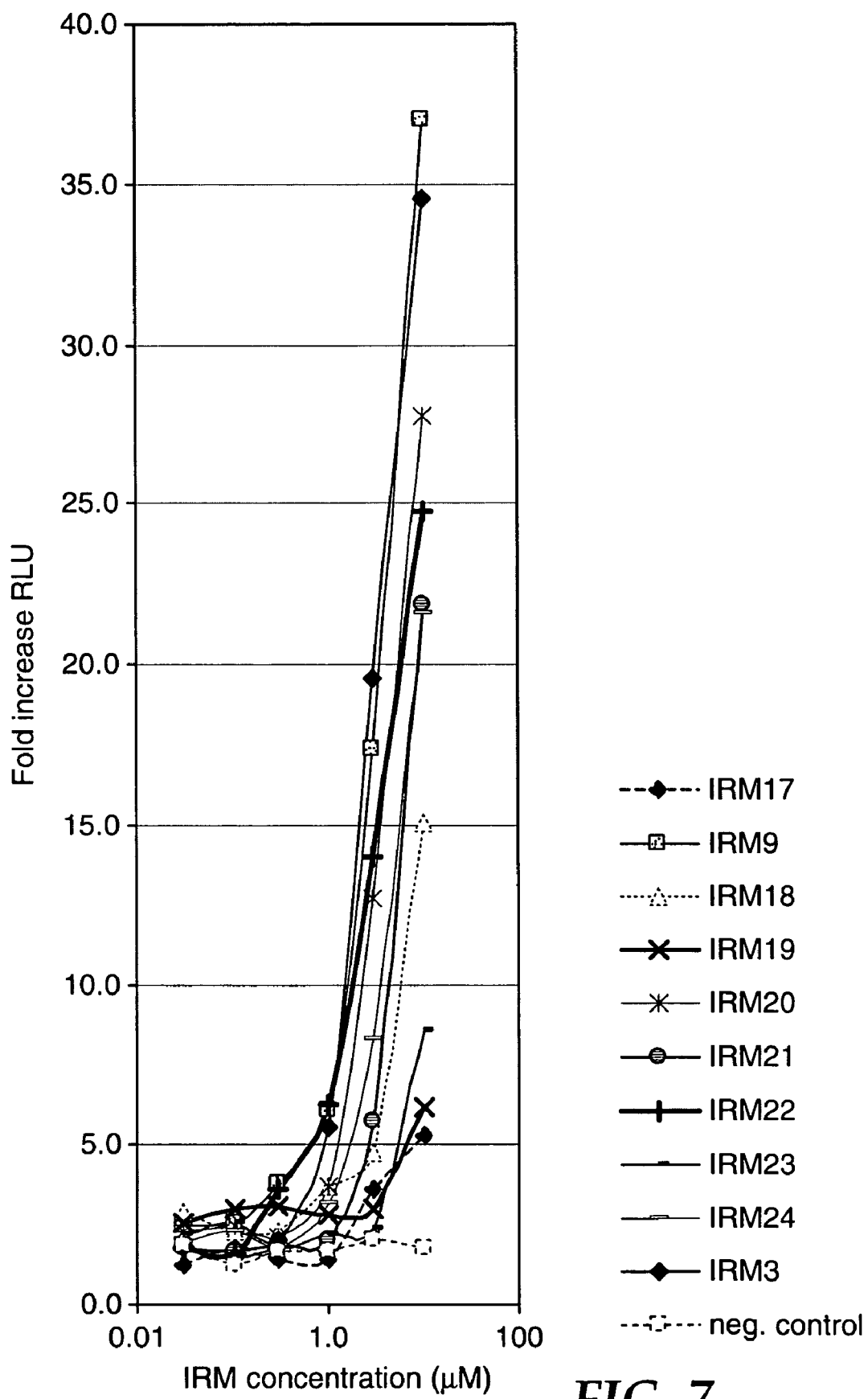
FIG. 7 is a line graph showing activation of TLR8 in HEK293 cells by certain TLR8 agonists.
Figure 8:
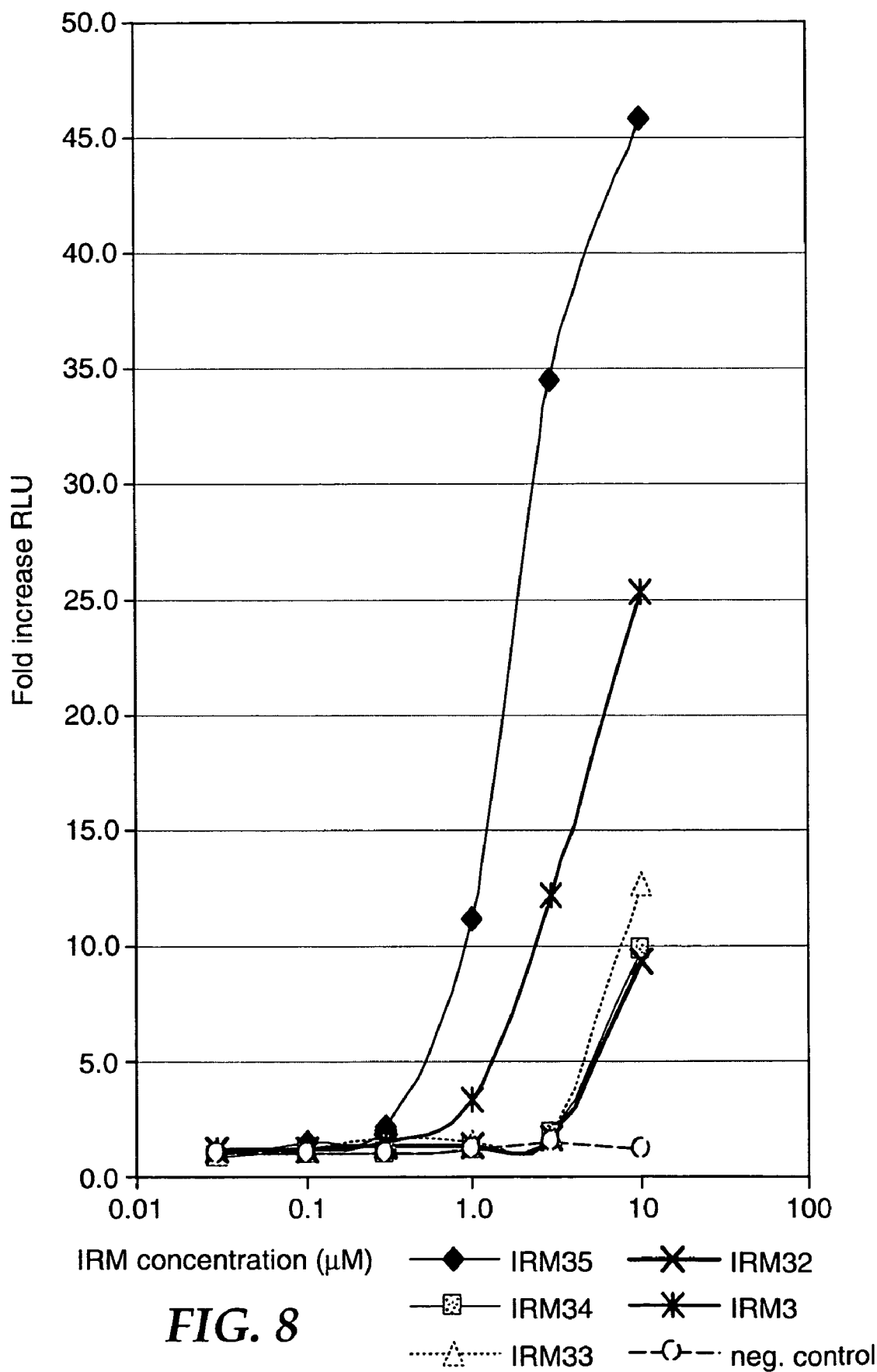
FIG. 8 is a line graph showing activation of TLR8 in HEK293 cells by certain TLR8 agonists.
Figure 9:
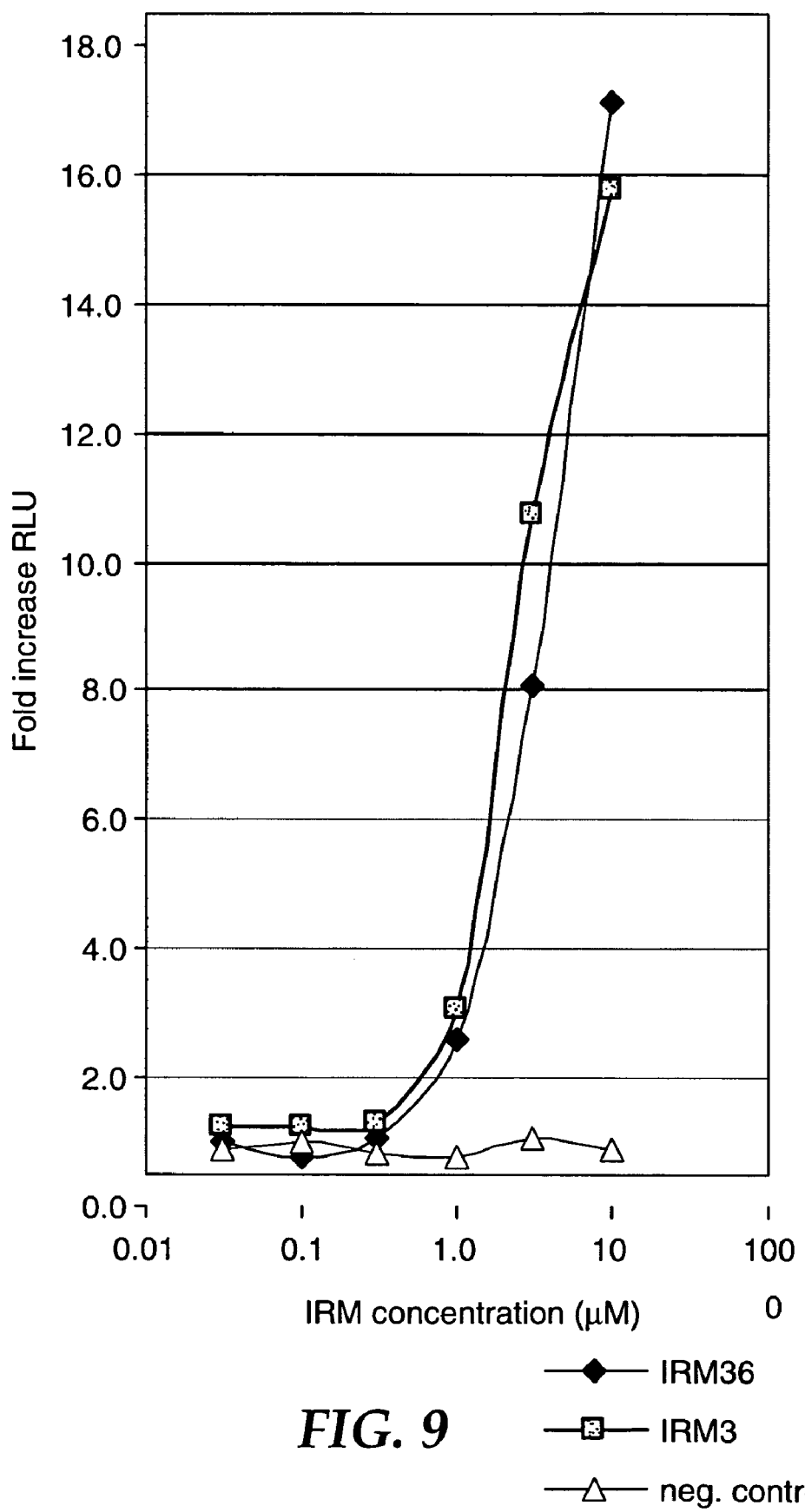
FIG. 9 is a line graph showing activation of TLR8 in HEK293 cells by certain TLR8 agonists.
Figure 10:
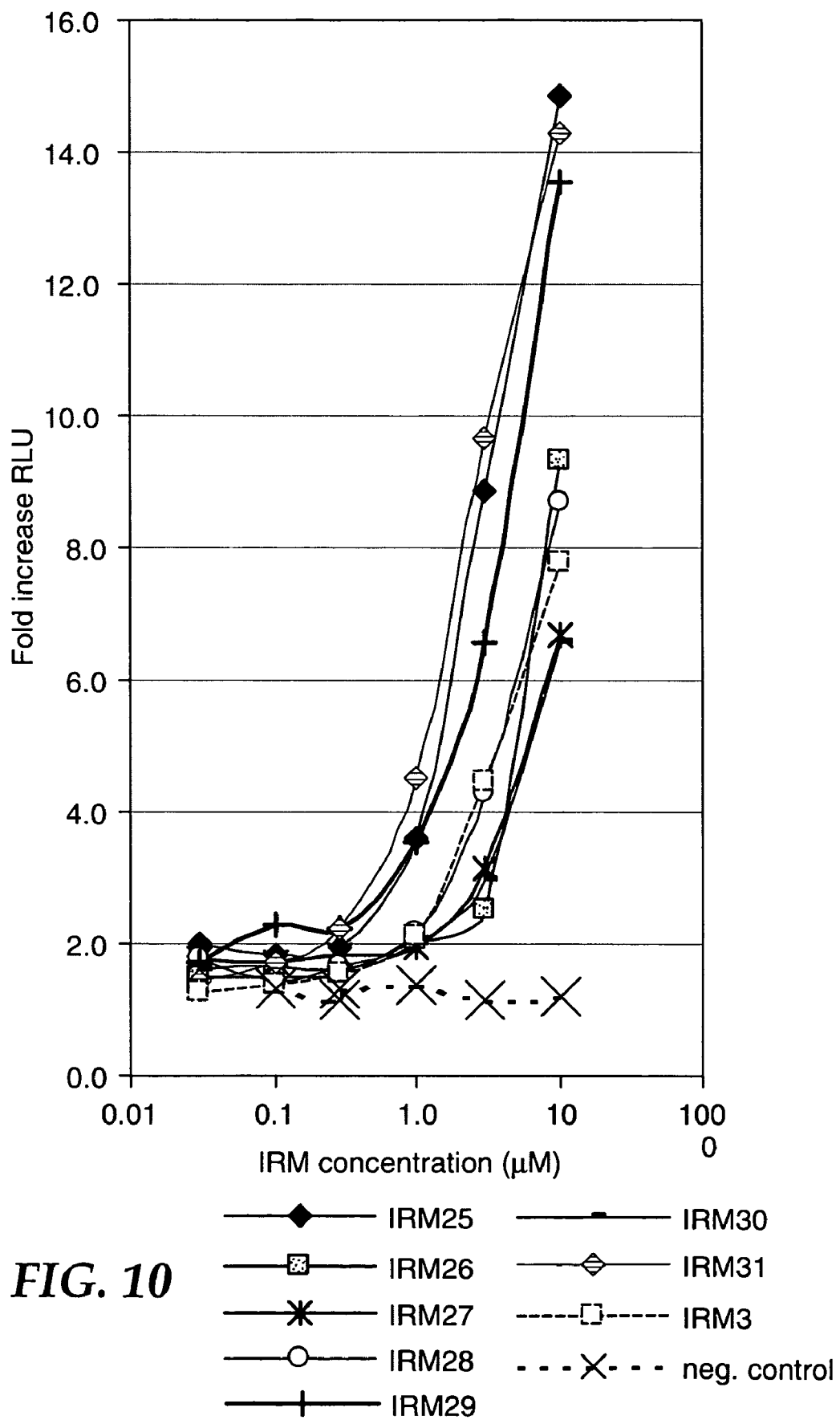
FIG. 10 is a line graph showing activation of TLR8 in HEK293 cells by certain TLR8 agonists.
Figure 11:
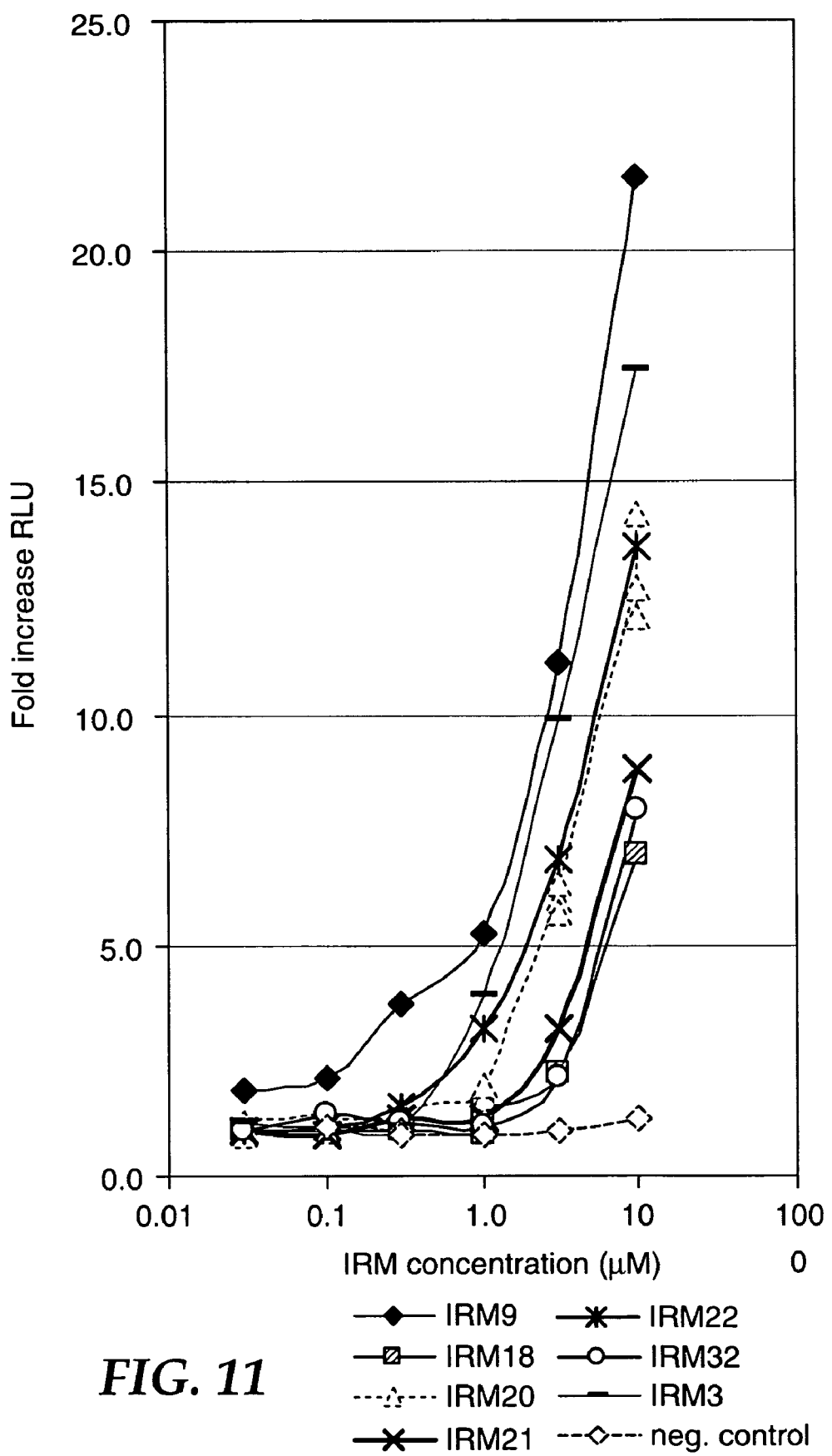
FIG. 11 is a line graph showing activation of TLR8 in HEK293 cells by certain TLR8 agonists.

Cytokine analysis was performed as described in Example 2. Results are shown in FIGS. 5 and 6.

Example 5

TLR8 Agonists Induce Dose Dependent TLR8-Mediated Cellular Responses in HEK293 Cells HEK293 cells were transfected as described in Example 1. HEK293 cultures were incubated with IRM compound or a negative control compound (1,5-dihydro-1-(2-methylpropyl)-4H-imidazo[4,5-c]quinolin-4-one, U.S. Pat. No. 4,698,348, Example 71) at concentrations of 0.1 μM, 0.3 μM, 1.0 μM, 3.0 μM, 10 μM, or 30 μM, or a vehicle control. Cultures were otherwise incubated as described in Example 1. Luciferase signals were read in RLU (Relative Luciferase Units) as described in Example 1. Results are shown in FIGS. 7-11 and Table 3.

TABLE 3

| TLR8 Agonist | Conc. (μM) | Fold increase over vehicle | TLR8 Agonist | Conc. (μM) | Fold increase over vehicle |
|---|---|---|---|---|---|
| IRM43 | 0.1 | 2.3 | IRM58 | 0.1 | 0.7 |
|  | 0.3 | 2.3 |  | 0.3 | 0.8 |
|  | 1.0 | 3.3 |  | 1.0 | 0.9 |
|  | 3.0 | 2.1 |  | 3.0 | 3.2 |
|  | 10 | 5.6 |  | 10 | 6.9 |
|  | 30 | 17.0 |  | 30 | 7.8 |
| IRM40 | 0.1 | 1.0 | IRM52 | 0.1 | 1.2 |
|  | 0.3 | 0.9 |  | 0.3 | 2.1 |
|  | 1.0 | 0.9 |  | 1.0 | 4.1 |
|  | 3.0 | 1.3 |  | 3.0 | 5.8 |
|  | 10 | 3.1 |  | 10 | 7.8 |
|  | 30 | 16.4 |  | 30 | 9.3 |
| IRM56 | 0.1 | 1.2 | IRM41 | 0.1 | 0.7 |
|  | 0.3 | 1.8 |  | 0.3 | 0.9 |
|  | 1.0 | 5.9 |  | 1.0 | 1.0 |
|  | 3.0 | 10.0 |  | 3.0 | 3.3 |
|  | 10 | 24.4 |  | 10 | 12.7 |
|  | 30 | 27.9 |  | 30 | 25.4 |
| IRM51 | 0.1 | 1.9 | IRM47 | 0.1 | 0.9 |
|  | 0.3 | 3.8 |  | 0.3 | 0.8 |
|  | 1.0 | 11.9 |  | 1.0 | 1.1 |
|  | 3.0 | 15.0 |  | 3.0 | 1.7 |
|  | 10 | 21.5 |  | 10 | 4.9 |
|  | 30 | 22.4 |  | 30 | 12.5 |
| IRM50 | 0.1 | 1.8 | IRM46 | 0.1 | 0.9 |
|  | 0.3 | 2.1 |  | 0.3 | 1.1 |
|  | 1.0 | 2.2 |  | 1.0 | 1.4 |
|  | 3.0 | 4.1 |  | 3.0 | 1.7 |
|  | 10 | 11.7 |  | 10 | 3.9 |
|  | 30 | 21.1 |  | 30 | 7.3 |
| IRM49 | 0.1 | 1.1 | IRM44 | 0.1 | 0.9 |
|  | 0.3 | 1.4 |  | 0.3 | 1.1 |
|  | 1.0 | 2.0 |  | 1.0 | 1.0 |
|  | 3.0 | 3.8 |  | 3.0 | 0.9 |
|  | 10 | 7.0 |  | 10 | 2.5 |
|  | 30 | 15.5 |  | 30 | 12.5 |
| IRM57 | 0.1 | 1.4 | IRM42 | 0.1 | 1.0 |
|  | 0.3 | 1.7 |  | 0.3 | 0.9 |
|  | 1.0 | 3.1 |  | 1.0 | 1.3 |
|  | 3.0 | 7.2 |  | 3.0 | 3.8 |
|  | 10 | 10.4 |  | 10 | 13.2 |
|  | 30 | 12.5 |  | 30 | 26.0 |
| IRM55 | 0.1 | 0.7 | IRM39 | 0.1 | 0.9 |
|  | 0.3 | 1.1 |  | 0.3 | 1.1 |
|  | 1.0 | 1.0 |  | 1.0 | 1.2 |
|  | 3.0 | 2.9 |  | 3.0 | 1.5 |
|  | 10 | 7.2 |  | 10 | 6.8 |
|  | 30 | 9.9 |  | 30 | 18.0 |
| IRM54 | 0.1 | 0.9 | IRM38 | 0.1 | 0.8 |
|  | 0.3 | 0.9 |  | 0.3 | 0.8 |
|  | 1.0 | 1.2 |  | 1.0 | 1.3 |
|  | 3.0 | 2.6 |  | 3.0 | 3.8 |
|  | 10 | 5.9 |  | 10 | 6.9 |
|  | 30 | 9.2 |  | 30 | 7.8 |
| IRM53 | 0.1 | 0.9 | IRM37 | 0.1 | 0.7 |
|  | 0.3 | 1.0 |  | 0.3 | 0.9 |
|  | 1.0 | 1.4 |  | 1.0 | 1.0 |
|  | 3.0 | 2.0 |  | 3.0 | 3.2 |
|  | 10 | 3.6 |  | 10 | 5.2 |
|  | 30 | 7.7 |  | 30 | 11.8 |
| IRM61 | 0.1 | 1.0 | IRM48 | 0.1 | 0.9 |
|  | 0.3 | 1.1 |  | 0.3 | 0.6 |
|  | 1.0 | 2.9 |  | 1.0 | 1.1 |
|  | 3.0 | 6.7 |  | 3.0 | 1.2 |
|  | 10 | 10.3 |  | 10 | 8.2 |
|  | 30 | 9.4 |  | 30 | 9.5 |

TABLE 3-continued

| TLR8 Agonist | Conc. (µM) | Fold increase over vehicle | TLR8 Agonist | Conc. (µM) | Fold increase over vehicle |
|---|---|---|---|---|---|
| IRM60 | 0.1 | 1.1 | IRM45 | 0.1 | 1.5 |
|  | 0.3 | 1.0 |  | 0.3 | 2.5 |
|  | 1.0 | 1.1 |  | 1.0 | 6.7 |
|  | 3.0 | 2.7 |  | 3.0 | 12.1 |
|  | 10 | 6.2 |  | 10 | 17.0 |
|  | 30 | 9.1 |  | 30 | 24.3 |
| IRM59 | 0.1 | 1.0 |  |  |  |
|  | 0.3 | 1.3 |  |  |  |
|  | 1.0 | 2.1 |  |  |  |
|  | 3.0 | 5.5 |  |  |  |
|  | 10 | 9.5 |  |  |  |
|  | 30 | 9.8 |  |  |  |

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A pharmaceutical composition comprising a Toll-like receptor 8 (TLR8) agonist that comprises a 2-aminopyridine fused to a five membered nitrogen-containing heterocyclic ring, or a pharmaceutically acceptable salt thereof, in an amount effective to modulate at least one TLR8-mediated cellular signaling pathway in combination with a pharmaceutically acceptable carrier.

2. The pharmaceutical composition of claim 1 wherein the TLR8 agonist is a substituted imidazoquinoline amine.

3. The pharmaceutical composition of claim 1 wherein the TLR8 agonist is a tetrahydroimidazoquinoline amine.

4. The pharmaceutical composition of claim 1 wherein the TLR8 agonist is an imidazopyridine amine.

5. The pharmaceutical composition of claim 1 wherein the TLR8 agonist is a 1,2-bridged imidazoquinoline amine.

6. The pharmaceutical composition of claim 1 wherein the TLR8 agonist is a 6,7-fused cycloalkylimidazopyridine amine.

7. The pharmaceutical composition of claim 1 wherein the TLR8 agonist is an imidazonaphthyridine amine.

8. The pharmaceutical composition of claim 1 wherein the TLR8 agonist is a tetrahydroimidazonaphthyridine amine.

9. The pharmaceutical composition of claim 1 wherein the TLR8 agonist is an oxazoloquinoline amine.

10. The pharmaceutical composition of claim 1 wherein the TLR8 agonist is a thiazoloquinoline amine.

11. The pharmaceutical composition of claim 1 wherein the TLR8 agonist is an oxazolopyridine amine.

12. The pharmaceutical composition of claim 1 wherein the TLR8 agonist is a thiazolopyridine amine.

13. The pharmaceutical composition of claim 1 wherein the TLR8 agonist is an oxazolonaphthyridine amine.

14. The pharmaceutical composition of claim 1 wherein the TLR8 agonist is a thiazolonaphthyridine amine.

15. The pharmaceutical composition of claim 1 wherein the TLR8 agonist is a 6-, 7-, 8-, or 9-aryl or heteroaryl substituted imidazoquinoline amine.

16. The pharmaceutical composition of claim 1 wherein the TLR8 agonist is a 1H-imidazo dimer fused to a pyridine amine, quinoline amine, tetrahydroquinoline amine, naphthyridine amine, or tetrahydronaphthyridine amine.

17. The pharmaceutical composition of claim 10, wherein the thiazoloquinoline amine is 2-propylthiazolo[4,5-c]quinolin-4-amine.

* * * * *